United States Patent
Levine

(10) Patent No.: US 7,158,829 B1
(45) Date of Patent: *Jan. 2, 2007

(54) METHOD AND APPARATUS FOR IMPROVING SPECIFICITY OF ATRIAL TACHYCARDIA DETECTION TECHNIQUES IN DUAL-UNIPOLAR OR DUAL-BIPOLAR IMPLANTABLE CARDIAC STIMULATION SYSTEMS

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 447 days.

This patent is subject to a terminal disclaimer.

(21) Appl. No.: 10/728,511

(22) Filed: Dec. 5, 2003

(51) Int. Cl.
A61N 1/368 (2006.01)
A61B 5/04 (2006.01)

(52) U.S. Cl. .................. 607/17; 607/25; 607/123; 600/510

(58) Field of Classification Search .................. 607/14, 607/17, 25, 123
See application file for complete search history.

(56) References Cited

U.S. PATENT DOCUMENTS

| | | | |
|---|---|---|---|
| 4,856,523 A | 8/1989 | Sholder et al. ............. 607/17 |
| 4,944,298 A | 7/1990 | Sholder ................. 607/14 |
| 5,144,949 A | 9/1992 | Olson ................. 607/17 |
| 5,331,966 A | 7/1994 | Bennett et al. | |
| 5,366,488 A | 11/1994 | Franberg et al. | |
| 5,441,523 A | 8/1995 | Nappholz ............. 607/14 |
| 5,466,254 A | 11/1995 | Helland ............. 607/123 |
| 5,522,855 A | 6/1996 | Hoegnelid ............. 607/9 |
| 5,549,649 A | 8/1996 | Florio et al. ............. 607/15 |
| 5,591,214 A | 1/1997 | Lu ................. 607/9 |
| 5,658,320 A | 8/1997 | Betzold et al. | |
| 5,720,295 A | 2/1998 | Greenhut et al. | |
| 5,788,717 A | 8/1998 | Mann et al. | |
| 6,047,213 A | 4/2000 | Sirokman et al. | |
| 6,128,533 A | 10/2000 | Florio et al. ............. 607/9 |
| 6,311,089 B1 | 10/2001 | Mann et al. | |
| 6,421,564 B1 * | 7/2002 | Yerich et al. ............. 607/9 |
| 6,434,424 B1 | 8/2002 | Igel et al. | |
| 6,477,415 B1 * | 11/2002 | Yerich et al. ............. 607/9 |
| 6,477,419 B1 | 11/2002 | Levine et al. | |
| 6,516,225 B1 | 2/2003 | Florio ................. 607/9 |
| 6,625,490 B1 * | 9/2003 | McClure et al. ............. 607/9 |

(Continued)

OTHER PUBLICATIONS

Johan Brandt et al. "Far Field QRS Complex Sensing via the Atrial Pacemaker Lead. I. Mechanisms, Consequences, Differential Diagnosis and Countermeasures in AAI and VDD/DDD Pacing," PACE, vol. 11 (Oct. 1998), pp. 1432-1438.

(Continued)

Primary Examiner—Robert E. Pezzuto
Assistant Examiner—Tammie K. Heller

(57) ABSTRACT

Techniques are provided for allowing Automatic Mode Switching (AMS) to be exploited within dual unipolar systems employing Combipolar sensing. Relative refractory windows are opened within both the atrial and ventricular refractory periods for the purposes of determining the atrial rate using Combipolar sensing logic. In this manner, T-waves occurring during the relative refractory windows are excluded from the atrial rate calculation, whereas any P-waves occurring during the relative refractory windows are counted, thereby achieving a more accurate atrial rate calculation, particularly at high atrial rates, and thus permitting AMS to be enabled along with Combipolar sensing in the dual unipolar lead system. An alternative technique is provided for use in dual unipolar systems not initially set to a Combipolar Sensing mode, which also achieves more accurate atrial rate calculation at high atrial rates. Additional techniques are provided for use in dual bipolar systems. An improved Combipolar sensing logic is also provided.

15 Claims, 15 Drawing Sheets

U.S. PATENT DOCUMENTS

| | | | |
|---|---|---|---|
| 6,650,931 | B1 | 11/2003 | McClure et al. |
| 6,711,438 | B1 | 3/2004 | McClure et al. |
| 6,731,980 | B1 * | 5/2004 | Mouchawar et al. ........... 607/9 |
| 6,907,287 | B1 | 6/2005 | Bevan et al. |
| 6,980,861 | B1 * | 12/2005 | Kleine .......................... 607/30 |
| 2006/0004418 | A1 | 1/2006 | Stahmann et al. |

OTHER PUBLICATIONS

Mark D. Gabry et al., "Comparison of Myopotential Interference in Unipolar-Bipolar Programmable DDD Pacemakers," PACE, vol. 10 (Nov.-Dec. 1987), pp. 1322-1330.

W. Irnich et al., "Filter Characteristics of Pacemaker Amplifiers," Medical and Biological Engineering (Nov. 1975), pp. 889-893.

P.A. Levine et al., "Automatic Mode Switching in the Pacesetter Trilogy DR+ and Trilogy DC+ Pulse Generators," in Sethi KK (ed), Proceedings of the VI Asian Pacific Symposium on Cardiac Pacing and Electrophysiology, 1997, publ: Monduzzi Editore S.p.A., Bologna, Italy, pp. 167-173.

P.A. Levine et al., "Implementation of Automatic Mode Switching in Pacesetter's Trilogy DR+ And Affinity DR Pulse Generators," Herzschrittmacher Elektrophysiology 10, Suppl 1 (1999), 146-157.

Paul A. Levine, M.D., Dual Chamber and Dual Chamber Rate Modulated Management Options for the Pacemaker Patient with Recurrent Paroxysmal Supraventricular Tachycardias, Pacesetter Inc., a St. Jude Medical Company, Sylmar CA (1995).

Uwe K.H. Wiegand et al. "Should Unipolar Leads be Implanted in the Atrium? A Holter Electrocardiographic Comparison of the Threshold Adapted Unipolar and High Sensitive Bipolar Sensing," PACE, vol. 21 (Aug. 1998), pp. 1601-1608.

* cited by examiner

METHOD AND APPARATUS FOR IMPROVING SPECIFICITY OF ATRIAL TACHYCARDIA DETECTION TECHNIQUES IN DUAL-UNIPOLAR OR DUAL-BIPOLAR IMPLANTABLE CARDIAC STIMULATION SYSTEMS

CROSS-REFERENCE TO RELATED APPLICATIONS

This application is related to copending U.S. patent applications: 1) Ser. No. 10/728,459, filed Dec. 5, 2003, titled "Method and Apparatus for Improving Specificity of Atrial Tachycardia Detection Techniques in Dual-Unipolar or Dual-Bipolar Implantable Cardiac Stimulation"; 2) Ser. No. 10/728,500, filed Dec. 5, 2003, titled "Method and Apparatus for Improving Specificity of Atrial Tachycardia Detection Techniques in Dual-Unipolar or Dual-Bipolar Implantable Cardiac Stimulation"; and 3) Ser. No. 10/728,659, filed Dec. 5, 2003, titled "Method and Apparatus for Improving Specificity of Atrial Tachycardia Detection Techniques in Dual-Unipolar or Dual-Bipolar Implantable Cardiac Stimulation".

FIELD OF THE INVENTION

The invention generally relates to implantable cardiac stimulation devices, such as pacemakers or implantable cardioverter/defibrillators ("ICDs") and, in particular, to techniques for processing intracardiac electrocardiogram (EGM) signals to facilitate recognition of atrial tachyarrhythmias in dual-unipolar or dual-bipolar systems.

BACKGROUND

A pacemaker is a medical device for implant within a patient that recognizes various arrhythmias such as an abnormally slow heart rate (bradycardia) or an abnormally fast heart rate (tachycardia) and delivers electrical pacing pulses to the heart in an effort to remedy the arrhythmias. An ICD is a device, also for implant within a patient that additionally recognizes atrial fibrillation (AF) or ventricular fibrillation (VF) and delivers electrical shocks to terminate the fibrillation.

Pacemakers and ICDs carefully monitor characteristics of the heart such as the heart rate to detect arrhythmias, discriminate among different types of arrhythmias, identify appropriate therapy, and determine when to administer the therapy. The heart rate is tracked by examining electrical signals that result in the contraction and expansion of the chambers of the heart. The contraction of atrial muscle tissue is a result of the atrial depolarization or electrical activation of the atrial tissue manifested as a P-wave in a surface electrocardiogram (ECG). The EGM is a recording of the electrical signal from within the heart and, in the case of the atrium, is referred to as an atrial EGM. The contraction of ventricular muscle tissue follows the electrical depolarization of the ventricle, which is manifest on the ECG by an R-wave (sometimes referred to as the "QRS complex") and as sharp deflection within a ventricular EGM termed the intrinsic deflection. Recovery of the cardiac electrical potential is manifest as a T-wave on the ECG. With the T-wave, the active cardiac contraction ceases and the ventricle begins to relax and dilate allowing the ventricle to expand and fill with blood in preparation for the next cardiac contraction or heartbeat. A similar phase involving the atrial tissue occurs but usually does not result in a detectable signal on the ECG because it is a smaller signal proportional to the P-wave amplitude and coincides with and is obscured by the QRS complex. The sequence of electrical events that represent P-waves, followed by R-waves, followed by T-waves can be detected within EGM signals sensed using pacing leads implanted inside the heart.

One commonly used type of lead is the unipolar lead, which includes a single electrode at or near its tip. A sense amplifier detects electrical voltage differentials between the electrode and the external body or housing of the pacemaker. In a dual-chamber, dual-unipolar pacing system, one unipolar lead is inserted within the atria and another within the ventricles, from which the device derives separate atrial and ventricular channel EGM signals. A problem with unipolar leads is that, because the sense amplifier detects the voltage differential between the tip of the lead and the housing of the pacemaker, the detection antenna is large, thereby allowing the system to detect extracardiac signals and significant electrical signals from the opposite cardiac chamber (termed "far-field") as well as the intended atrial or ventricular EGM signals. A far-field signal is a signal originating from the opposite cardiac chamber but detected by the sensing lead nonetheless, delivered to the sense amplifier within the pacemaker from the channel to which the lead is connected and potentially interpreted as arising from that chamber. For example, the atrial EGM signal derived from the atrial lead may include significant ventricular signals and, in the case of single chamber pacing systems, may be reset and recycled by this detected but inappropriate signal. Note also that the tissue mass in the ventricle is relatively large, resulting in a large electrical signal in either the bipolar or the unipolar sensing configurations. As far-field signals tend to be of low amplitude, far-field signals recordable on the ventricular channel are commonly managed by making the ventricular channel less sensitive. However, signals arising from the atrium usually have relatively low amplitudes. As such, the pacemaker must be programmed to a very sensitive setting in order to appropriately detect near-field intrinsic atrial signals, resulting in possible detection of far-field signals. Indeed, keeping the atrial channel set to a very sensitive setting predisposes the detection of far-field signals.

Another commonly employed type of lead is the bipolar lead, which includes two electrodes mounted in close proximity to one another within the heart. Usually, one electrode is called the "tip" and the other the "ring." Typically, one bipolar lead is inserted within the atria and another within the ventricles, from which the device derives separate atrial and ventricular signals. An atrial sense amplifier detects electrical voltage differentials between the tip and ring electrodes of the atrial lead. A ventricular sense amplifier detects electrical voltage differentials between the tip and ring electrodes of the ventricular lead. The use of bipolar sensing leads improves the signal-to-noise ratio and allows the sensitivity to be set to a very sensitive setting without significant risk of inadvertent detection of extracardiac or far-field events. However, bipolar leads are more complex than unipolar leads and, based on their track record, are perceived as being less reliable than unipolar leads and hence are not preferred by all physicians. Further, even in circumstances wherein a bipolar lead is employed, it may need to be operated in a unipolar mode. For example, if a mechanical problem occurs within a bipolar lead, the lead may need to be operated in a unipolar mode. Hence, far-field sensing problems may arise even in circumstances where bipolar leads are implanted.

In an attempt to provide the advantages of bipolar sensing using simpler unipolar leads, some state-of-the-art devices employ a combined unipolar/bipolar sensing technique, referred to as Combipolar sensing. ("Combipolar" is a trademark of St. Jude Medical.) With Combipolar sensing, unipolar leads are positioned within the heart, one in the atria and one in the ventricles. A ventricular channel EGM signal is generated in the same manner as with conventional unipolar sensing wherein electrical voltage differentials are detected between the tip of the ventricular lead and the housing of the device. However, the atrial channel of the EGM signal is generated by detecting cross-chamber voltage differentials between electrodes at the tips of the atrial and ventricular leads. A logic system internal to the pacemaker determines whether events appearing within the cross-chamber signal are atrial events or ventricular events. In this regard, an event sensed on both the atrial and ventricular channels is regarded as a ventricular event. An event sensed only on the atrial channel is regarded as a true atrial event. An event sensed only on the ventricular channel is regarded as being of extracardiac origin. For a more complete description of Combipolar systems, see U.S. Pat. No. 5,522,855 (Hoegnelid), incorporated herein by reference. Initially, the term "Combipolar sensing" was applied only to dual unipolar systems wherein the cross-chamber signal was sensed V-tip to A-tip. Herein, however, the term "Combipolar sensing" more generally applies to any system employing an atrial-to-ventricular cross-chamber signal for use in detecting atrial events, in combination with a ventricular unipolar signal for detecting ventricular events. The term "combined unipolar/bipolar sensing" is also used herein to refer to Combipolar sensing.

Thus, Combipolar sensing allows some of the advantages of bipolar sensing to be exploited within implanted able systems employing unipolar leads. However, one disadvantage is that, because the atrial signal is detected based upon voltage differentials between the tips of the atrial and ventricular leads, ventricular signals are sensed as "near-field" signals. As a result, intrinsic ventricular signals are recorded on the atrial channel. This is not a problem where the intrinsic ventricular signals are also detected on the ventricular channel since the logic of the Combipolar system will thereby regard the signals as being ventricular signals, but if an intrinsic signal arising in the ventricle is not detected on the ventricular channel but only on the atrial channel, it will be treated as a P-wave. Such may be the case with the T-wave, which may coincide with the ventricular refractory period (VRP)—a period of time when the ventricular channel does not respond to intrinsic signals (at least within some devices.)

More specifically, within a refractory period the device does not process electrical signals during a predetermined interval of time either for all device functions (an absolute refractory period) or for selected device functions (a relative refractory period). As an example, upon detection of an R-wave on the ventricular channel, a post-ventricular atrial refractory period (PVARP) is initiated on the atrial channel. Traditionally, devices were disconnected from inputs during the absolute portion of the refractory period and therefore could not sense any events. More recent devices allow sensing of atrial events throughout the PVARP, though the device does to respond to events sensed within the PVARP. Typically, a first portion of the PVARP comprises a post ventricular atrial blanking (PVAB) interval wherein the pacemaker can detect signals on the atrial channel but does not use the signals for any purpose. The PVAB is provided to prevent the device from erroneously responding to a far-field R-wave on the atrial channel. The PVARP concludes with a relative refractory period during which the pacemaker continues to ignore all signals detected on the atrial channel as far as triggering or inhibiting pacing functions is concerned, but not for other functions, such as detecting rapid atrial rates or recording diagnostic information. A total atrial refractory period (TARP) is defined as the period of time including an atrioventricular AV delay, any AV delay extension and the PVARP. The sum of the AV delay and the PVARP defines the fastest atrial rate that can be detected to still trigger a ventricular output in a 1:1 relationship.

Exemplary VRP, PVAB, PVARP and TARP periods and their affect on detecting rapid atrial rates are illustrated in FIGS. 1 and 2, which show stylized representations of a surface electrocardiogram (ECG) and atrial and ventricular EGM channels detected using Combipolar sensing. FIG. 1 illustrates the case of a normal sinus rhythm. FIG. 2 illustrates an episode of atrial tachyarrhythmia. The P-waves and R-waves appear within the atrial and ventricular IEGMs as sharp discrete complexes. The T-wave appears as a discrete signal but of lower amplitude and lower frequency response. The lower frequency components may result in this signal being effectively negated by the filters in the sensing circuit of most bradycardia pacemakers but not by those of ICDs which tend to have a broader band-pass filter to facilitate recognition of low amplitude, low frequency signals associated with ventricular tachyarrhythmias.

Referring first to FIG. 1, the PVAB interval, which begins upon detection of an R-wave on the ventricular channel, is set to a duration sufficient to cover the R-wave such that the R-wave is not detected in the atrial channel. The terminal portion of the PVARP interval that extends beyond the PVAB coincides with the T-wave. In standard Combipolar sensing algorithms, all signals detected during the terminal portion of the PVARP are ignored for the purposes of atrial rate detection. Hence, the T-wave, if capable of being detected on the atrial channel based on its amplitude and frequency content is nevertheless ignored on the atrial channel and an accurate determination of the atrial rate can be achieved, at least during normal sinus rhythm. However, during the episode of atrial tachyarrhythmia shown in FIG. 2, P-waves occurring during the terminal portion of the PVARP are also ignored along with the T-wave thereby resulting in a significant underestimate of the true atrial rate.

Accurate detection of rapid atrial rates is required, for example, for the purposes of enabling Automatic Mode Switching (AMS) algorithms wherein the pacemaker is capable of automatically switching between a tracking mode such as the VDD or DDD and a nontracking mode such as VVI or DDI mode based on whether the atrial rate exceeds an atrial tachycardia detection rate (ATDR) threshold. (Note that the term AMS is sometimes used to refer to only the actual switch from the tracking mode to the non-tracking mode. Herein the term in used to more generally refer to the capability of automatically switching back and forth between tracking and non-tracking modes based on atrial rate.) VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type. Details regarding AMS may be found in the following patents: U.S. Pat. Nos. 5,441,523; 5,591,214; 5,144,949; 4,856,523; 4,944,298; each of which is incorporated herein by reference. See also Levine et al., "Implementation Of Automatic Mode Switching In Pacesetter's Trilogy DR+ And Affinity DR Pulse Generators", Herzschrittmacher Elektrophysiology 10 (1999) 5, S46–S57.

The atrial rate underestimate described with reference to FIG. 2 can result in a failure to trigger a mode switch to a nontracking mode in dual unipolar VDD or DDD systems or to recognize high atrial rates in a nontracking mode such as DDI. Although, nontracking devices typically do not provide for therapeutic intervention (such as AMS) because the pathologic atrial arrhythmia is not capable of being tracked, it is nevertheless desirable that the presence of the atrial arrhythmia be recognized and its duration documented for diagnostic purposes.

To ensure that the atrial rate is properly assessed, an improved Combipolar technique may be employed wherein signals detected during the terminal portion of the PVARP are used for the purposes of atrial rate calculation. In other words, P-waves detected during the relative refractory portion of the PVARP are counted in the determination of the atrial rate. However, with this improved Combipolar technique, the T-wave occurring during the terminal portion of the PVARP may also be detected on the atrial channel. Although detection of the T-wave on the atrial channel during an episode of atrial tachyarrhythmia may not be a significant problem, detection of the T-wave on the atrial channel during normal sinus rhythm will result in a significantly erroneous high atrial rate calculation. Indeed, the detected atrial rate will typically be twice the actual rate. If AMS is enabled, the erroneously high atrial rate will frequently result in unnecessary mode switching to a nontracking mode. If an atrial high rate counter is enabled, inappropriate high atrial rates may be reported.

However, standard Combipolar sensing logic, which identifies signals detected on both the atrial and ventricular channels as being of ventricular origin, would not be capable of eliminating the T-wave since, in this scenario, the T-wave is not detected on the ventricular channel because it occurs during the absolute portion of the VRP during which no sensing is permitted on the ventricular channel (at least in some devices). Even if the T-wave occurs after the absolute portion of the VRP, the T-wave typically will not be detected on the ventricular channel because of band-pass filtering on the ventricular channel or because the sensitivity of the ventricular channel is set to a less sensitive setting that effectively eliminates T-waves. In contrast, the atrial channel is usually programmed to a very sensitive setting in order to detect pathologic atrial arrhythmias, which are often of a significantly lower amplitude signal than the sinus P-wave and the near-field T-wave. Hence, even if the T-wave occurs outside the VRP, the T-wave may be detected only on the atrial channel, particularly if different filters and/or sensitivities are utilized on the atrial and ventricular channels, resulting in further problems in accurate atrial rate detection. In certain dual-chamber ICDs, the atrial and ventricular channels both employ sense amplifiers with broad band-pass filters to facilitate detection of low amplitude, low frequency fibrillatory signals. This can result in significant T-wave oversensing. Hence, even with the improved Combipolar technique, inappropriate high atrial rates may be detected.

Thus, the true atrial rate cannot reliably be determined in many dual unipolar VDD and DDD systems, even with improved Combipolar sensing techniques, and AMS is therefore not enabled usually within such devices. Hence, it would be desirable to provide improved techniques for determining the true atrial rate so as to permit the use of AMS in dual unipolar VDD and DDD systems. It would also be desirable to provide improved techniques for determining the true atrial rate in DDI device using dual unipolar leads to permit detection of high atrial rates.

In addition, when using atrial bipolar leads circumstances can arise wherein T-wave oversensing becomes an issue despite T-wave filtering. FIG. 3 illustrates exemplary EGMs along with various event markers for a normal canine sinus rhythm yet wherein an implanted dual bipolar AMS pacemaker performs an unnecessarily mode switch to a non-tracking mode due to far-field T-wave sensing on the atrial channel. (More specially, the graph illustrates a sense amp signal derived from atrial tip-ring signals along with a raw ventricular tip-ring signal.) In the example, the atrial channel is programmed to a very sensitive setting (0.3 mV) and the ventricular channel programmed to a value ten times less sensitive (3.0 mV). The PVARP is shorter than the VRP and the far-field T-wave coincides with an atrial alert period but also with the VRP. Double arrows identify some of the far-field T-waves. The far-field T-wave on the atrial channel is a very discrete and relatively sharp complex having been processed by the sensing circuit. If standard Combipolar sensing logic were to be applied to the foregoing example in an effort to avoid the unnecessary mode switch, the rhythm would still be labeled an atrial tachycardia because the T-wave was sensed on the atrial channel but not the ventricular channel and so an inappropriate mode switch to a non-tracking mode would occur. In particular, under Combipolar sensing logic, the pacemaker properly identifies event 11 as being a true P-wave because it is only detected on the atrial channel. The pacemaker properly identifies event 13 as being a true R-wave because it appears on both the atrial and ventricular channels. However, the pacemaker incorrectly identifies T-wave 15 as a P-wave because (a) it coincides with the VRP and (b) the size of the signal is smaller than the programmed sensitivity on this channel. In other words, because of T-wave filtering, the T-wave is not sensed on the ventricular channel but is only sensed on the atrial channel. Hence, T-waves are misinterpreted as P-waves causing an inappropriate mode switch.

Accordingly, it would also be desirable to provide improved techniques for implementing Combipolar sensing in atrial bipolar systems so as to avoid far-field T-wave oversensing.

Atrial rate detection problems also arise in connection with atrial leads employed in bipolar configuration if placed in close anatomic proximity to the ventricle such that a large far-field R-wave is detected. Such positions include the coronary sinus and the low interatrial septum, both locations receiving increasing attention from implanting physicians as pacing from these locations may reduce the incidence of atrial arrhythmias. Hence, even in the bipolar sensing configuration, a large far-field signal may be detected resulting in inaccurate high atrial rate detection and inappropriate mode switches. Accordingly, it would also be desirable to provide improved techniques for implementing Combipolar sensing in atrial bipolar systems so as to avoid far-field R-wave oversensing.

SUMMARY

In accordance with a first embodiment, a technique is provided for use in determining an atrial heart rate within an implantable cardiac stimulation device wherein combined bipolar/unipolar sensing (i.e. Combipolar sensing) is normally employed to detect atrial events. In accordance with the technique, ventricular channel signals are sensed using unipolar sensing (e.g. V-tip to case) and atrial channel signals are sensed using Combipolar sensing (i.e. the signals are sensed using some cross-channel combination of electrodes such as A-tip to V-tip, A-ring to V-ring, A-ring to V-tip, A-tip to V-ring, V-tip to A-ring1 or V-ring to A-ring2.) Refractory periods are tracked within both the atrial and ventricular channel signals. The atrial rate is determined using Combipolar sensing logic applied to events sensed within the refractory periods as well as to events sensed outside the refractory periods. By opening both atrial and ventricular refractory periods for use in atrial rate determination, the atrial rate determination is more accurate. The improved accuracy allows AMS to be enabled within such devices. Preferably, any signals sensed with the refractory periods are only used in the assessment of the atrial rate if AMS is actually enabled. If AMS is not enabled, the atrial rate is instead assessed based only on events sensed outside the refractory periods.

By applying Combipolar sensing logic to events sensed within both the atrial and ventricular refractory periods, sensed events occurring simultaneously on the atrial and ventricular channel signals are excluded from the atrial rate determination. In this manner, events sensed on both channels during within the refractory periods are properly excluded from the atrial rate calculation, thereby achieving a more accurate atrial rate calculation than devices that would otherwise only open the atrial refractory period for sensing. Note that, although both the atrial and ventricular refractory periods are opened for use in atrial rate assessment, not all events occurring during the refractory periods are necessarily sensed. For example, events occurring during absolute blanking portions of the refractory periods are typically not sensed and hence are not used in the atrial rate calculation. Combipolar sensing may also be advantageously applied within the refractory period even in non-AMS devices, such as devices employing an atrial high rate detection diagnostic event counter operating in a DDI[R] or an AAI[R] mode. In other words, Combipolar sensing is employed passively to assist in the detection and documentation of high atrial rates so as to reduce the possibility that far-field sensing will contribute to a false diagnosis of atrial tachyarrhythmia.

In accordance with a second embodiment, a technique is provided for use in determining an atrial heart rate within an implantable cardiac stimulation device wherein dual unipolar sensing is ordinarily employed to detect all events. According to this embodiment, Combipolar sensing is selectively activated during the refractory periods to improve atrial rate determination. Briefly, atrial and ventricular refractory periods are tracked within atrial and ventricular channel signals. The atrial rate is determined using unipolar sensing applied to events detected outside the refractory periods and using combined unipolar/bipolar sensing logic applied to events sensed within the refractory periods. By activating Combipolar sensing during the refractory periods, high atrial rates can be more reliably tracked so as to avoid inappropriate mode switching. Preferably, Combipolar sensing is only activated if either AMS is enabled or if an atrial high rate detection diagnostic event counter is enabled. Otherwise, dual unipolar sensing is exclusively employed.

In accordance with a third embodiment, a technique is provided for use in determining an atrial heart rate within an implantable cardiac stimulation device wherein atrial bipolar sensing is ordinarily employed to detect all atrial events. As with the second embodiment, Combipolar sensing is selectively activated during the refractory periods to improve atrial rate determination. The atrial rate is determined using bipolar sensing applied to events detected outside the refractory periods and using combined unipolar/bipolar sensing logic applied to events sensed within the refractory periods. This technique is of particular value in systems wherein an atrial bipolar electrode is positioned in the coronary sinus so as to detect left atrial activity. The anatomic course of the coronary sinus runs between the left ventricle and left atrium. As such, even a bipolar lead commonly will detect a large ventricular signal. Utilizing Combipolar sensing if the lead is in the coronary sinus will then minimize inappropriate AMS and high atrial rate detection. Again, preferably, Combipolar sensing is only activated during the refractory period if either AMS is enabled or if an atrial high rate detection diagnostic event counter is enabled. Otherwise, atrial bipolar sensing is exclusively employed.

Additionally, a modified form of Combipolar sensing logic is preferably employed if an atrial bipolar lead is used, which seeks to exclude false P-waves based on their proximity to R-waves. Briefly, a determination is made as to whether a candidate P-wave occurs on the atrial channel within a selected period of time (e.g. 400 milliseconds (ms)) bracketing a detected R-wave. If not, the candidate P-wave is deemed to be a true P-wave. However, if so, a sensitivity of the ventricular channel is increased to be at least equal that of the atrial channel during the period of time bracketing the R-wave. A determination is then made as to whether an R-wave is detected on the ventricular channel within a second, shorter, period of time bracketing the P-wave (e.g. 50 ms). If not, the candidate P-wave is again deemed to be true P-wave. Otherwise, the P-wave is rejected as being a false P-wave. By exploiting the modified Combipolar sensing logic for use with an atrial bipolar lead, improved atrial rate determination is achieved.

Also preferably, the sensitivity of the ventricular channel is increased during the PVARP to be at least equal to that of the atrial channel. The ventricular sensitivity is selectively adjusted so as to prevent T-wave oversensing despite T-wave filtering. This technique effectively negates the potential for lack of ventricular sensing of a true T-wave due to the programmed sensitivity of the device. If the sensing circuits for both channels utilize a similar band-pass filter, the sensitivity is preferably increased on the ventricular channel to be equal that already programmed on the atrial channel. This increased sensitivity will only be in effect during the refractory period.

In accordance with a fourth embodiment, a technique is provided for use in determining an atrial heart rate within an implantable cardiac stimulation device wherein Combipolar sensing is selectively activated based on a comparison of the atrial rate against a threshold that is typically less than the ATDR. In accordance with the technique, standard refractory periods are tracked within atrial and ventricular channel signals sensed using a non-Combipolar sensing technique, e.g. unipolar or bipolar sensing. A previously determined atrial rate is compared against a predetermined threshold for the purposes of selecting an atrial rate determination technique. The predetermined threshold is typically about 20–30 beats per minute (bpm) below the ATDR. If the previously determined rate does not exceed the threshold, the atrial rate is updated based on events detected via the non-Combipolar sensing technique. However, if the atrial rate exceeds the threshold, the atrial rate is updated based on events detected using Combipolar sensing.

Preferably, as before, the ventricular sensitivity is sensitivity increased. However, with this technique, the ventricular sensitivity is only increased if all P-waves are deemed to be true P-waves under the Combipolar sensing technique. Then (if not already open) relative refractory windows periods are opened in the atrial and ventricular refractory periods and the duration of the ventricular refractory period is optionally reduced. A determination is then made as to whether all prior P-waves are still identified as true P-waves under the Combipolar sensing logic using the adjusted ventricular parameters. If not, the implanted device continues to assess the atrial rate using Combipolar sensing with the adjusted parameters until the atrial rate falls below the predetermined threshold. Otherwise, the device compares the atrial rate against a second, higher threshold (typically the ATDR) and, if it exceeds the second threshold, appropriate action is taken, such as switching to a non-tracking mode or initiating an atrial high rate diagnosis. Thus, with this technique, the activation of Combipolar sensing and the adjustment of the ventricular sensitivity only occur at high atrial rates. Note also that the Combipolar sensing technique logic employed depends upon the type of leads being used. If unipolar leads are employed, then otherwise conventional Combipolar sensing logic is employed. However, if bipolar leads are employed, the modified Combipolar technique summarized above is used wherein atrial events are identified based, in part, on their proximity to ventricular events.

Thus, in its various embodiments, the system improves atrial rate calculation so as to permit the use of AMS within systems that otherwise would not employ AMS and to reduce inappropriate mode switching within devices that do employ AMS. Other advantages and features of the various embodiments are described below.

BRIEF DESCRIPTION OF THE DRAWINGS

Further features and advantages of the various embodiments may be more readily understood by reference to the following description taken in conjunction with the accompanying drawings, in which:

FIGS. 9-1 and 9-2 depict a flow chart illustrating an alternative method performed by the system of FIG. 4 for use with dual unipolar leads to achieve improved atrial rate determination wherein Combipolar sensing is selectively activated during refractory periods;

FIGS. 10-1 and 10-2 depict a flow chart illustrating an alternative method performed by the system of FIG. 4 for use with dual bipolar leads;

FIGS. 12-1 and 12-2 depict a flow chart illustrating an alternative method performed by the system of FIG. 4 for use with either unipolar or bipolar leads wherein Combipolar sensing is only activated at high atrial rates so as to achieve improved atrial rate determination.

DETAILED DESCRIPTION OF THE ILLUSTRATIVE EMBODIMENTS

The following description is of the best mode presently contemplated for practicing the system. This description is not to be taken in a limiting sense but is made merely for the purpose of describing the general principles of the various embodiments. The scope of the invention should be ascertained with reference to the issued claims. In the description that follows, like numerals or reference designators will be used to refer to like parts or elements throughout. The system may be implemented using the implantable cardiac stimulation device illustrated in FIG. 4. An overview of the stimulation device is provided, followed by a detailed description of the methods according to illustrative embodiments.

Implantable Device Overview

Figure 4:
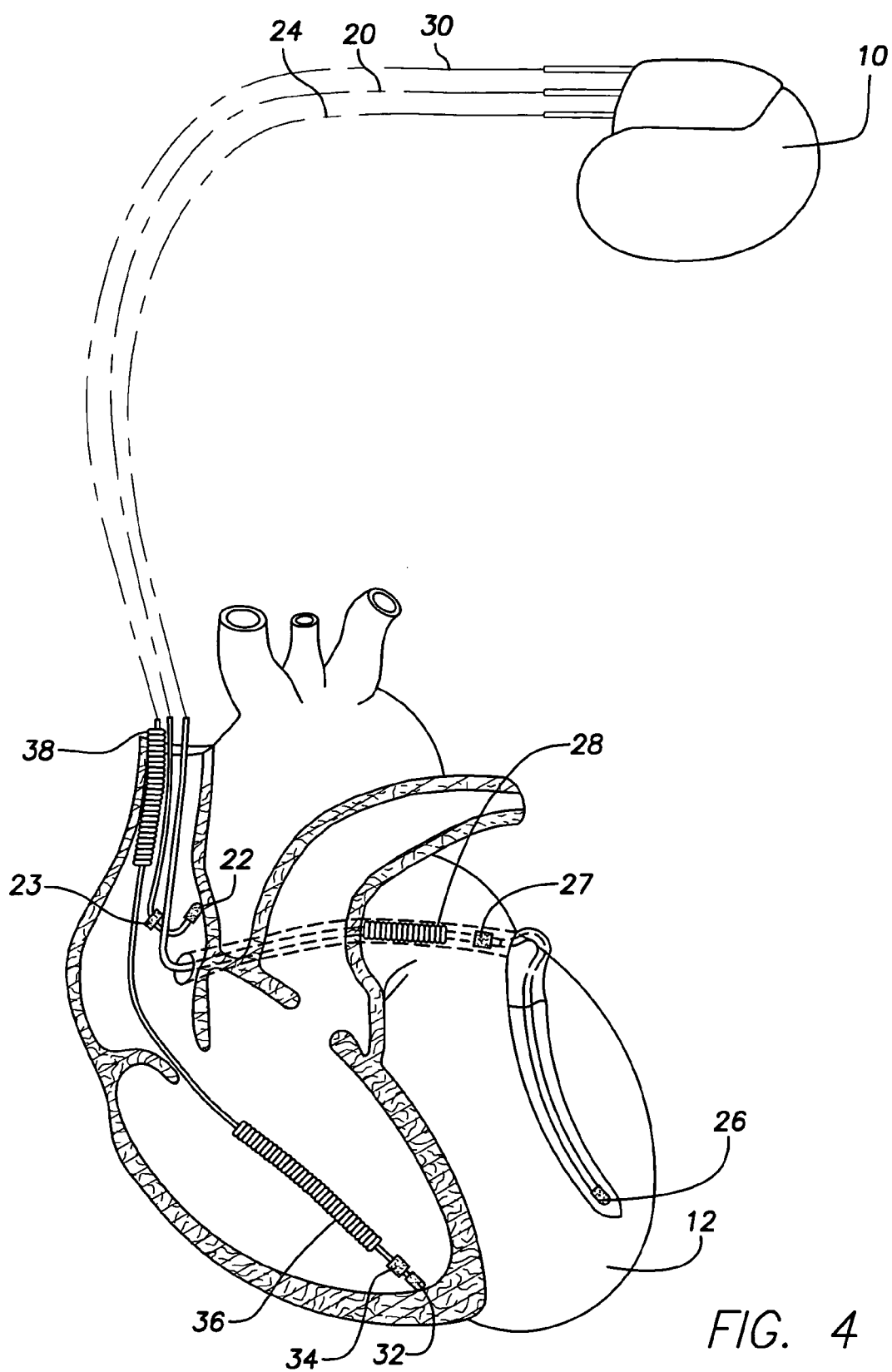
FIG. 4 is a simplified diagram illustrating an implantable stimulation device in electrical communication with at least three leads implanted into a heart for delivering multi-chamber stimulation and shock therapy including biatrial or biventricular sensing and pacing.
Figure 5:
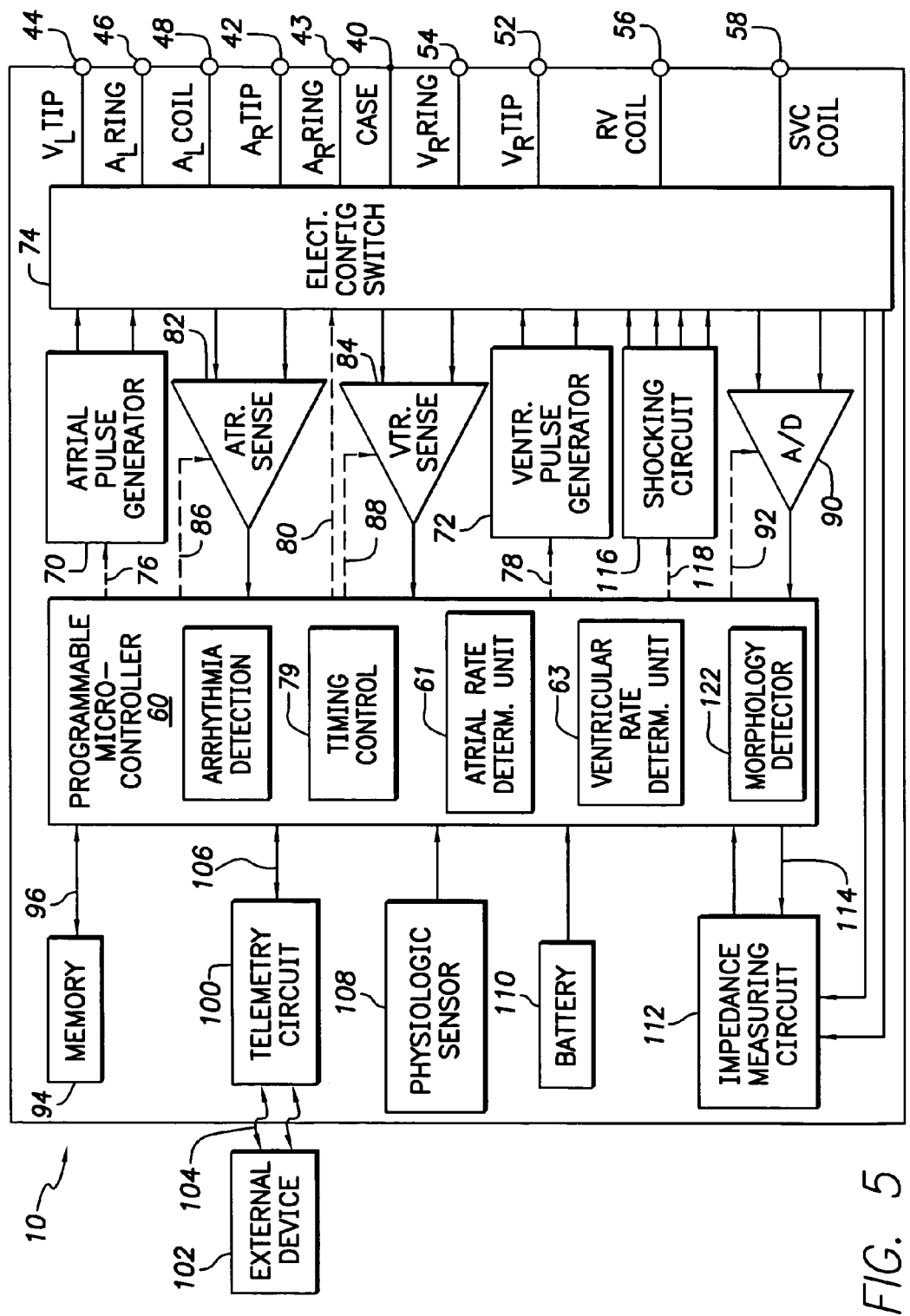
FIG. 5 is a functional block diagram of a multi-chamber implantable stimulation device illustrating the basic elements of a stimulation device which can provide cardioversion, defibrillation and pacing stimulation in four chambers of the heart and particularly illustrating improved atrial and ventricular rate determination units.

In FIG. 4, a simplified block diagram is shown of a dual-chamber implantable stimulation device 10, which is capable of treating both fast and slow arrhythmias with stimulation therapy, including cardioversion, defibrillation, and pacing stimulation. To provide atrial chamber pacing stimulation and sensing, the stimulation device 10 is shown in electrical communication with a patient's heart 12 by way of an implantable unipolar atrial lead 20 having an atrial tip electrode 22 implanted in the patient's atrial appendage and an atrial ring electrode 23. The stimulation device 10 is also in electrical communication with the patient's heart 12 by way of an implantable RV lead 30 having, in this embodiment, a RV tip electrode 32, an RV ring electrode 34, a RV (RV) coil electrode 36, and a superior vena cava (SVC) coil electrode 38. Typically, the ventricular lead 30 is transvenously inserted into the heart 12 so as to place the RV coil electrode 36 in the RV apex, and the SVC coil electrode 38 in the superior vena cava. Accordingly, the ventricular lead 30 is capable of receiving cardiac signals, and delivering stimulation in the form of pacing and shock therapy to the right ventricle. The stimulation device 10 is also in electrical communication with the patient's heart 12 by way of an implantable LV lead 24 having, in this embodiment, an LV tip electrode 26 and an LV ring electrode 27. Typically, the LV lead 24 is transvenously inserted into the Coronary Veins of the heart 12. Accordingly, the LV lead 24 is capable of receiving cardiac signals, and delivering stimulation in the form of pacing and shock therapy to the left ventricle. Additionally, an LV coil may be provided.

Figure 1:
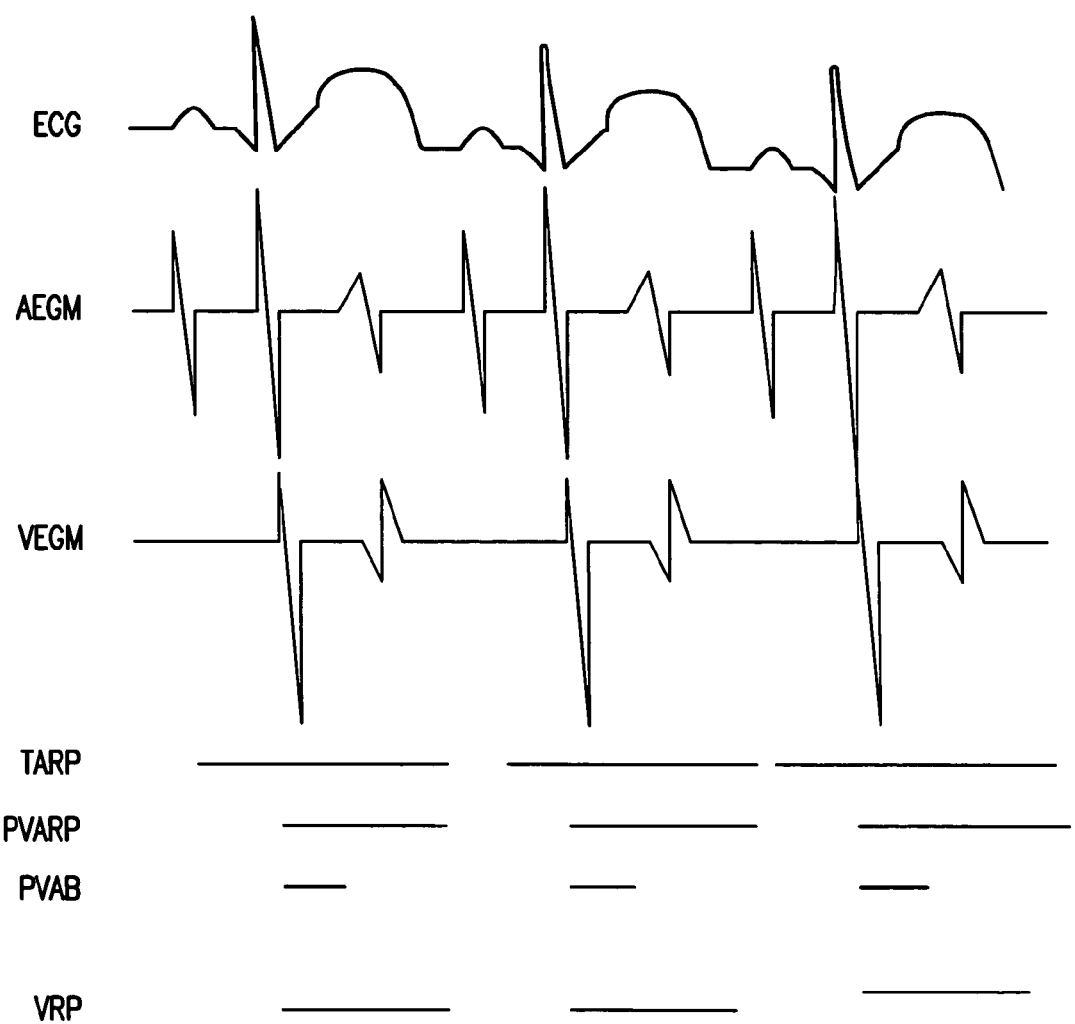
FIG. 1 is a graph illustrating exemplary atrial and ventricular channel EGM signals detected using traditional Combipolar sensing during normal sinus rhythm.

While unipolar leads are shown in FIG. 4, it is to be understood that bipolar leads could alternatively be employed, but used in a unipolar sensing mode or Combipolar sensing mode. Also, although three leads are shown in FIG. 1, it should also be understood that fewer or additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing and atrial or ventricular shocking therapy.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Additional terminals may be provided for use with RA rings, LV rings or an LV coil.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions is well known in the art.

Among other internal components, the microcontroller includes an atrial rate determination unit 61 and a ventricular rate determination unit 63. The atrial rate determination unit determines the atrial rate based on signals receive from the unipolar leads in accordance with techniques described in detail below with reference to FIGS. 5–8. The ventricular rate determination unit can be otherwise conventional.

As shown in FIG. 4, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes a timing control unit that controls the operation of the stimulation device timing of such stimulation pulses that is known in the art. The microcontroller 60 may also include an AutoCapture threshold detection system, though AutoCapture threshold detection system is not necessary.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, sets the polarity of the stimulation pulses by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity. The switch bank also permits the pacemaker to be set to either unipolar sensing or Combipolar sensing. For unipolar sensing, the V TIP and CASE terminals are connected to the ventricular sense amplifier for sensing a voltage differential there between and the A TIP and CASE terminals are connected to the atrial sense amplifier for sensing a voltage differential there between. For Combipolar sensing, the V TIP and CASE terminals are likewise connected to the ventricular sense amplifier but the A TIP and V TIP terminals are connected to the atrial sense amplifier for sensing a voltage differential between the tips of the atrial and ventricular leads.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers, 82 and 84, are connected to the microcontroller 60 which, in turn, inhibits the atrial and ventricular pulse generators, 70 and 72, respectively, in a demand fashion whenever cardiac activity is sensed in the respective chambers.

For arrhythmia detection, the system utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, activation of special algorithms such as automatic mode switch or high atrial rate episode logging, anti-tachycardia pacing, cardioversion shocks or defibrillation shocks, also known as "tiered therapy"). An arrhythmia detection unit of the microcontroller oversees arrhythmia detection.

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical and is shown only for completeness. The stimulation device additionally includes a battery 114 that provides operating power to all of the circuits shown in FIG. 4. For the stimulation device 10, which employs shocking therapy, the battery must be capable of operating at low current drains for long periods of time and then be capable of providing high-current pulses (for capacitor charging) when the patient requires a shock pulse (preferably, in excess of 2 A, at voltages above 200 V, for periods of 10 milliseconds or more). The battery 114 must also have a predictable discharge characteristic so that elective replacement time can be detected. Accordingly, the present system preferably employs lithium vanadium pentoxide batteries if implemented as an ICD and lithium iodine batteries if implemented as a pacemaker. As further shown in FIG. 4, the system preferably includes an impedance measuring circuit 120, which is enabled by the microcontroller 60 by a control signal 122. The impedance measuring circuit 120 is not critical and is shown for only completeness.

Depending upon the implementation, the device may function as an implantable cardioverter/defibrillator (ICD) device. That is, if it detects the occurrence of an arrhythmia, it automatically applies an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 joules), moderate (0.5 to 10 joules), or high energy (11 to 40 joules), as controlled by the microcontroller 60. Such shocking pulses are applied to the patient's heart through at least two shocking electrodes, as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to 40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The remaining figures include flow charts illustrating improved atrial rate determination methods, which permit the use of AMS and/or atrial high rate detection within the dual unipolar system described above or in an atrial bipolar system when at least one atrial lead is located in the coronary sinus or based on its anatomic location, is identified by the clinician as detecting a large far-field signal. In the flow charts, the various steps of the methods are summarized in individual "blocks". Such blocks describe specific actions or decisions that are made or carried out as the method proceeds. The flow charts presented herein provide the basis for a "control program" that may be used by the microcontroller (or equivalent) to effectuate the desired control of the stimulation device. Those skilled in the art may readily write such a control program based on the flow charts and other descriptions presented herein.

Dual Unipolar System with Atrial Combipolar Sensing Enabled

Figure 6:
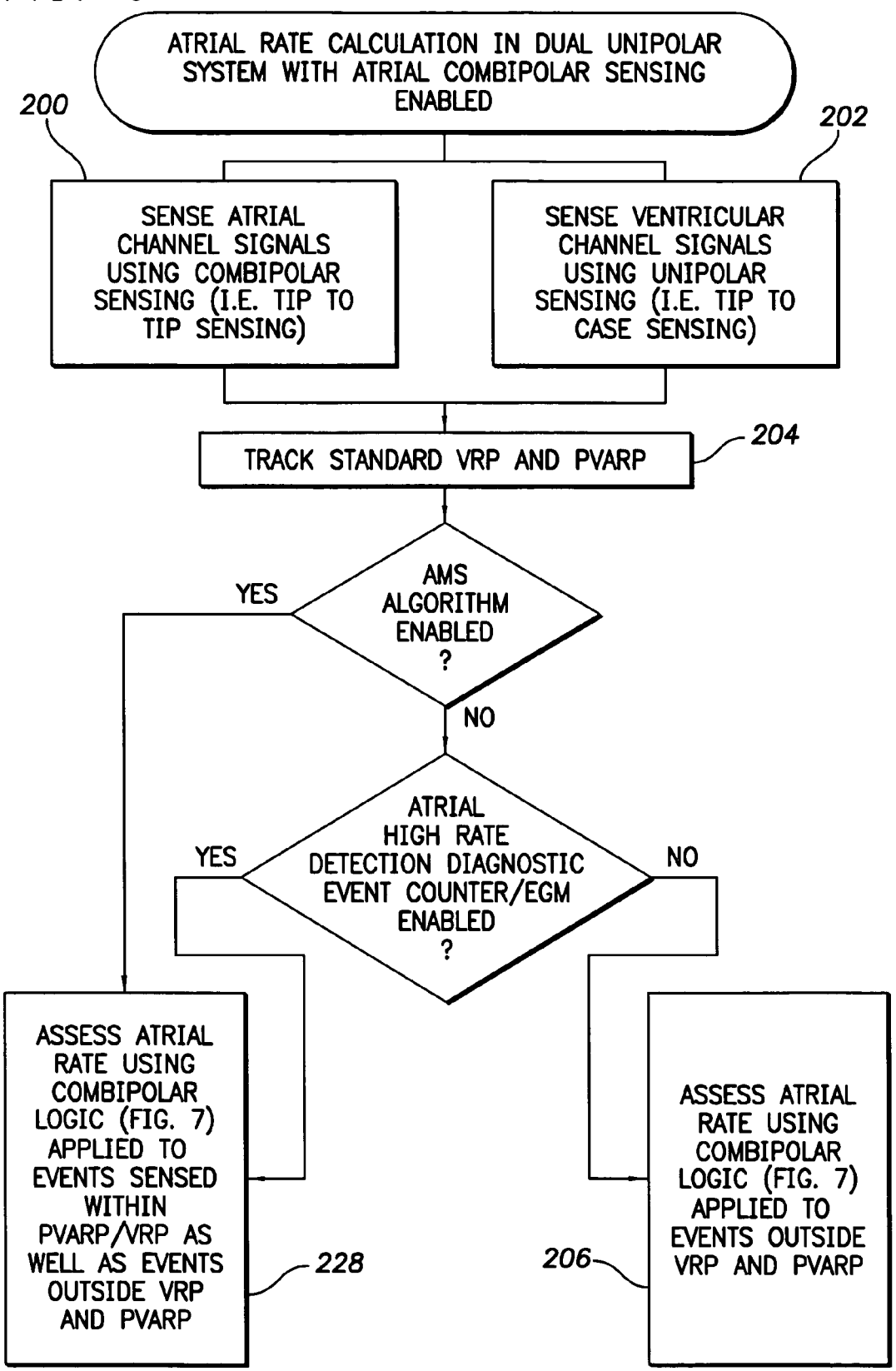
FIG. 6 is a flow chart illustrating a method performed by the atrial rate determination unit of FIG. 4 for achieving improved atrial rate determination during Combipolar sensing with dual unipolar leads.

Referring first to FIG. 6, a method for determining an atrial rate is illustrated for use by the pacemaker of FIG. 4, which employs dual unipolar leads, wherein the pacemaker is programmed to perform Combipolar sensing of atrial channel signals and unipolar sensing of ventricular channel signals. Initially, at step 200, the pacemaker begins sensing an atrial channel EGM signal based on a voltage differential detected between the tip of the atrial lead and the tip of the ventricular lead in accordance with Combipolar sensing. Simultaneously, at step 202, the pacemaker begins sensing a ventricular channel EGM signal based on a voltage differential detected between the tip of the ventricular lead and the body of the pacemaker in accordance with unipolar sensing. Upon detection of an R-wave on the ventricular channel, the pacemaker begins tracking a VRP on the ventricular channel and a PVARP on the atrial channel, step 204. Thereafter, processing depends on whether AMS (wherein AMS refers to the capability to automatically switch between tracking and nontracking modes based on the atrial rate) is enabled and whether an atrial high rate diagnostic event counter or EGM diagnostic unit is enabled. The atrial high rate diagnostic event counter/EGM records atrial events occurring above a maximum tracking rate and above a programmable value selected by the clinician.

If AMS is not currently enabled and an atrial high rate diagnostic event counter/EGM diagnostic unit is also not enabled, then the atrial rate determination unit of the pacemaker determines the atrial rate at step 206 in accordance with standard Combipolar sensing logic wherein any events occurring within PVARP and VRP are simply excluded. If AMS is enabled, then the atrial rate is instead determined at step 228 using a modified version of the Combipolar sensing, which additionally takes into account events sensed within the PVARP. The modified Combipolar technique is also applied in any mode wherein an atrial high rate diagnostic event counter/EGM diagnostic unit is enabled (such as DDI[R] or AAI[R]). Although not specifically shown, after the atrial rate has been updated at step 228, a mode switch may be performed based on the update atrial rate (assuming AMS is enabled). In this manner, the pacemaker is capable of calculating atrial rates beyond the maximum tracking rate. This is in contrast with conventional techniques that exclude all atrial events occurring during the entire PVARP and hence cannot calculate an atrial rate higher than the maximum tracking rate. This is also in contrast to any Combipolar technique that opens a relative refractory window within the PVARP but not within the VRP and hence mislabels T-wave as P-waves. By permitting accurate calculation of high atrial rates, AMS can be reliably implemented within dual unipolar systems. Note that some P-waves may occur during an absolute blanking portion of the PVARP and hence not be sensed. For this reason, the atrial rate determination during atrial tachyarrhythmia is not necessarily perfectly accurate, but it is certainly more accurate than with techniques that disregard all P-waves during the PVARP.

Figure 7:
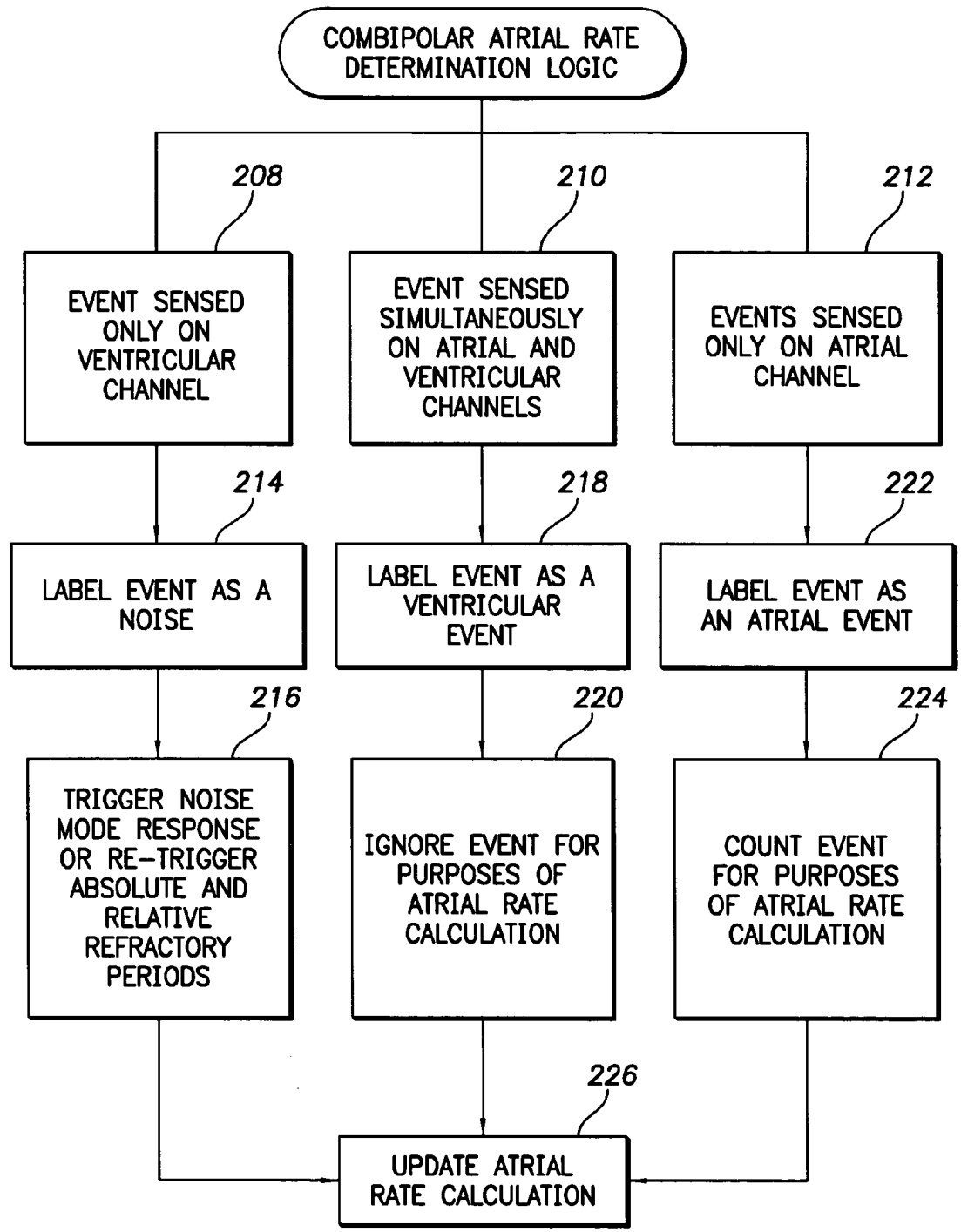
FIG. 7 is a flow chart illustrating Combipolar sensing logic for use with the method of FIG. 6.

Note that, in this embodiment, standard Combipolar logic is employed—regardless of whether step 206 is employed or step 228. Standard Combipolar sensing logic is illustrated in FIG. 7. Briefly, upon sensing of an electrical event on either the atrial or ventricular channels, the pacemaker determines whether the event is sensed a) only on the ventricular channel (step 208), b) simultaneously on the atrial and ventricular channels (step 210), or c) only on the atrial channel (step 212). If sensed only on the ventricular channel, the event is labeled as noise (step 214) and ignored for the purposes of atrial rate calculation (step 216). If sensed simultaneously on the atrial and ventricular channels, the event is labeled as a ventricular event (step 218) and again ignored for the purposes of atrial rate calculation (step 220). If sensed only on the atrial channel, the event is labeled as a true atrial event, i.e. a P-wave, (step 222) and is counted for the purposes of atrial rate calculation (step 224). Once the event has been properly labeled, the pacemaker updates the atrial rate calculation at step 226.

Figure 8:
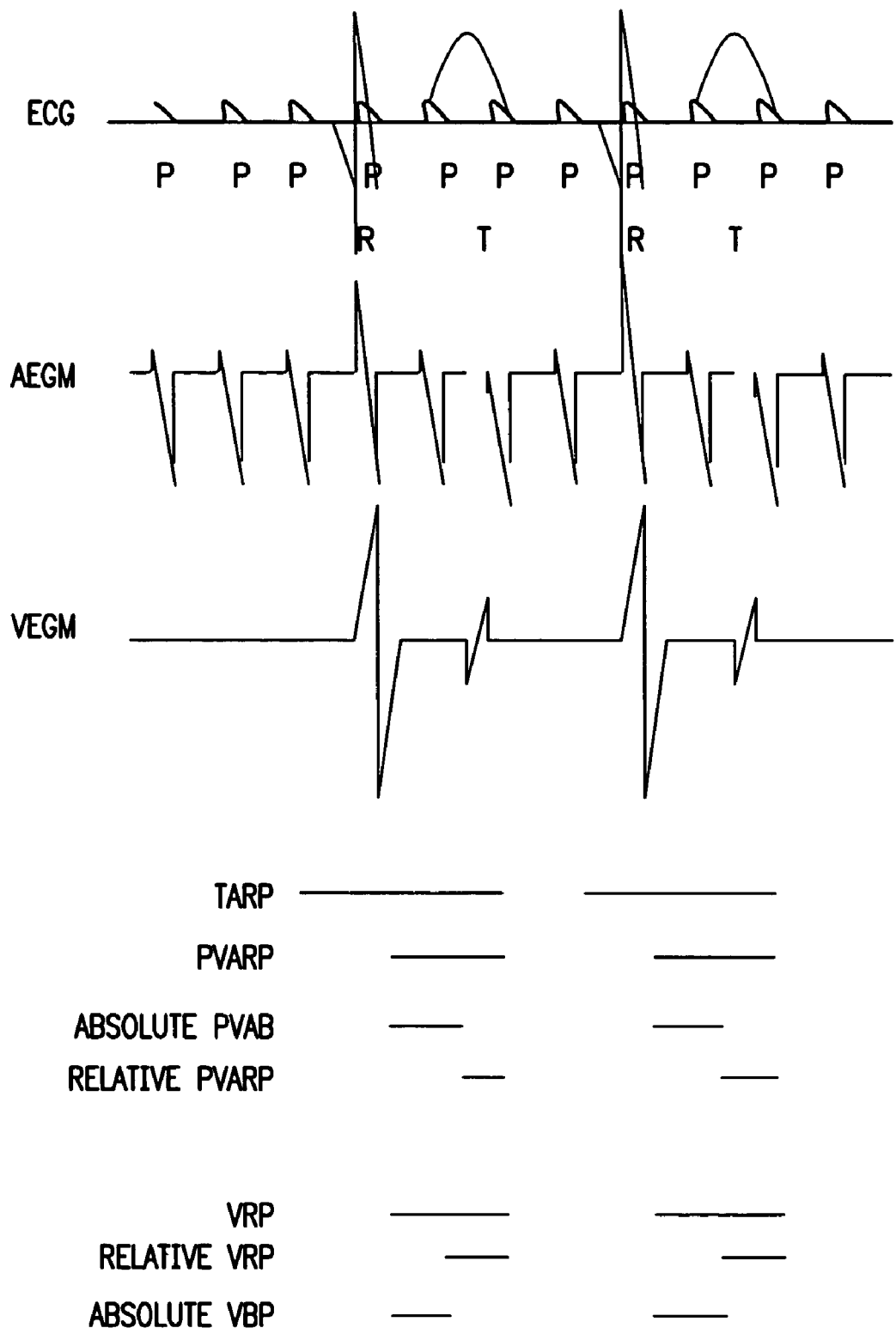
FIG. 8 is a graph illustrating exemplary atrial and ventricular channel EGM signals detected during an episode of atrial tachyarrhythmia and particularly illustrating relative refractory windows within both the atrial and ventricular refractory periods.

By applying Combipolar sensing logic to events within the refractory periods, as well as to other events, improved atrial rate calculation is achieved. This is illustrated in FIG. 8, which shows the VRP and PVARP periods along with stylized representations of a surface ECG and atrial and ventricular EGM channels detected using Combipolar sensing during an episode of atrial tachyarrhythmia. The VRP and PVARP are subdivided into absolute and relative portions. In accordance with standard terminology, the absolute portion of the PVARP is referred to as the PVAB and the relative portion of the PVARP is referred to as the relative PVARP. The absolute portion of the VRP is referred to herein as an absolute ventricular blanking period (VBP) and the relative portion of the VRP is referred to herein as a relative VRP. The VRP is split so that the T-wave is likely to occur during the relative VRP, thereby permitting detection via Combipolar sensing, whereas the QRS complex occurs during the absolute VRP. In this regard, it is assumed that the ventricles remain at a normal sinus rhythm and are unaffected by the atrial tachyarrhythmia. The PVARP is likewise split so that the T-wave is coincides with the relative PVARP, thereby permitting detection, whereas the QRS complex occurs during the PVAB and is not sensed. Note that the duration of the entire PVARP and VRP intervals are not shortened in view of the atrial tachyarrhythmia. Rather the entire intervals remain at normal length, but now include relative refractory portions during which sensing occurs. The figure also shows a total atrial refractory period (TARP) that represents the AV delay plus the PVARP.

Due to the atrial tachyarrhythmia, at least some P-waves occur during the PVARP. Those detected during the relative PVARP are labeled as atrial events by the Combipolar sensing logic and are used to update the atrial rate calculation. T-waves occur during the relative VRP and the relative PVARP and are thereby detected on both the atrial and ventricular channels. Hence, the T-waves are labeled as ventricular events by the Combipolar sensing logic and not counted in the atrial rate determination (step 220 of FIG. 7) thus improving atrial rate determination.

Although not explicitly shown, with the technique of FIG. 6 (and within all techniques described herein), the actual atrial rate may be calculated in accordance with filtered atrial rate interval (FARI) averaging techniques wherein all atrial events are counted, including both sensed and paced atrial events, whether captured or not. Filtered atrial rate techniques are discussed in U.S. Pat. No. 5,549,649 to Florio, et al., entitled "Programmable Pacemaker Including an Atrial Rate Filter for Deriving a Filtered Atrial Rate Used for Switching Pacing Modes" and in U.S. Pat. No. 6,128,533 also to Florio, et al., entitled "Pacemaker With Automatic PVARP Adjustment During Automatic Mode Switching", which are both incorporated by reference herein. In addition, the example of FIG. 6 employs dual unipolar leads wherein the atrial-to-ventricular cross-chamber signal is sensed A-tip to V-tip. The techniques can also be applied to other lead systems wherein the cross-chamber signal is sensed using some other cross-channel combination of electrodes such as A-ring to V-ring, A-ring to V-tip, A-tip to V-ring or if multiple atrial ring electrodes are provided, V-tip to A-ring$_1$ or V-ring to A-ring$_2$.

Hence, FIGS. 6–8 provide an overview of a technique for use in devices that employ Combipolar sensing but would otherwise not enable AMS due to atrial rate calculation errors. By extending Combipolar sensing to apply to events within the refractory periods, improved atrial rate determination is achieved so as to permit AMS to be enabled. Next, a technique is described for use in AMS devices that ordinarily employ unipolar sensing.

Dual Unipolar Lead System with Atrial Unipolar Sensing Enabled

Figure 2:
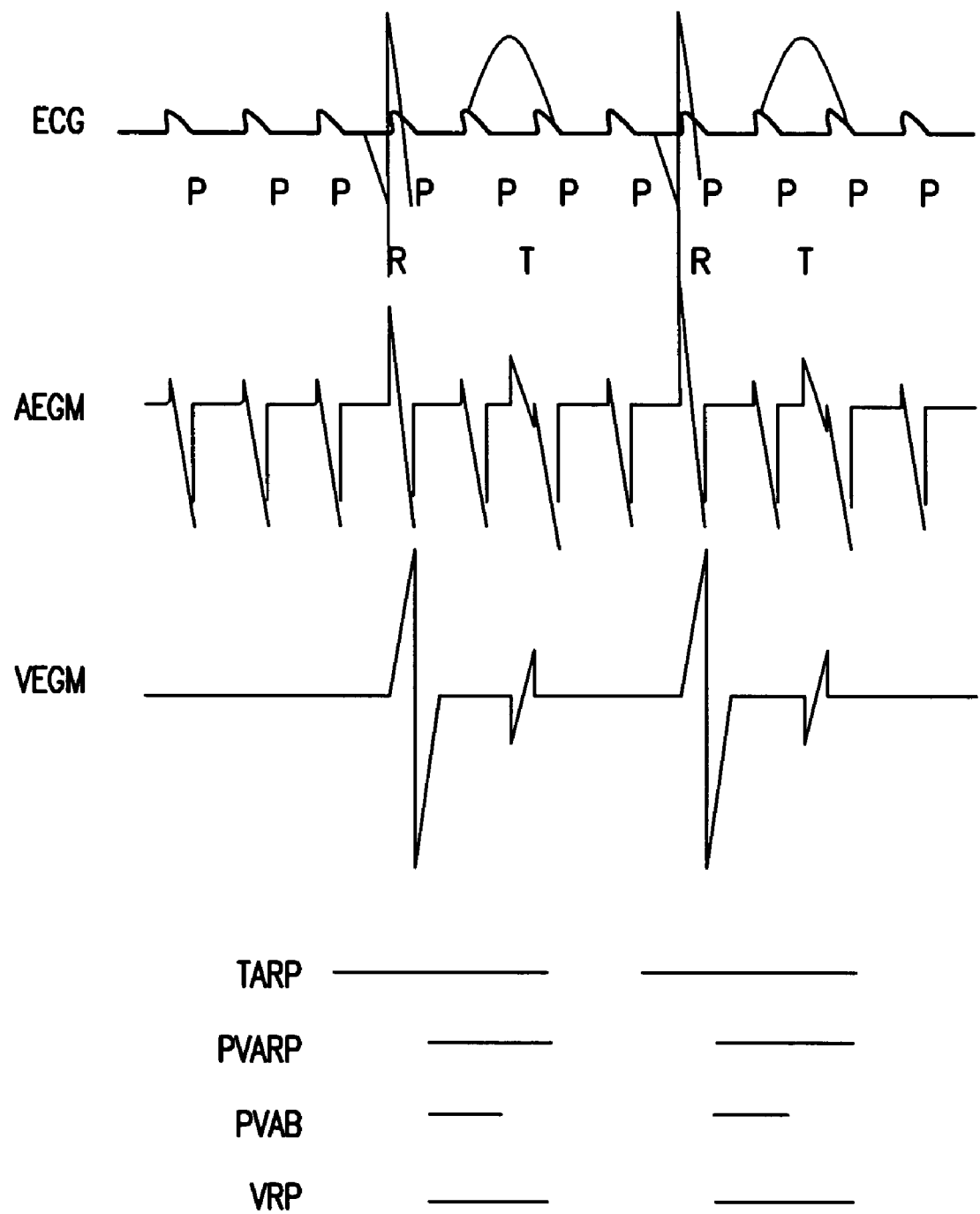
FIG. 2 is a graph illustrating exemplary atrial and ventricular channel EGM signals detected using traditional Combipolar sensing during an episode of atrial tachyarrhythmia.
Figure 3:
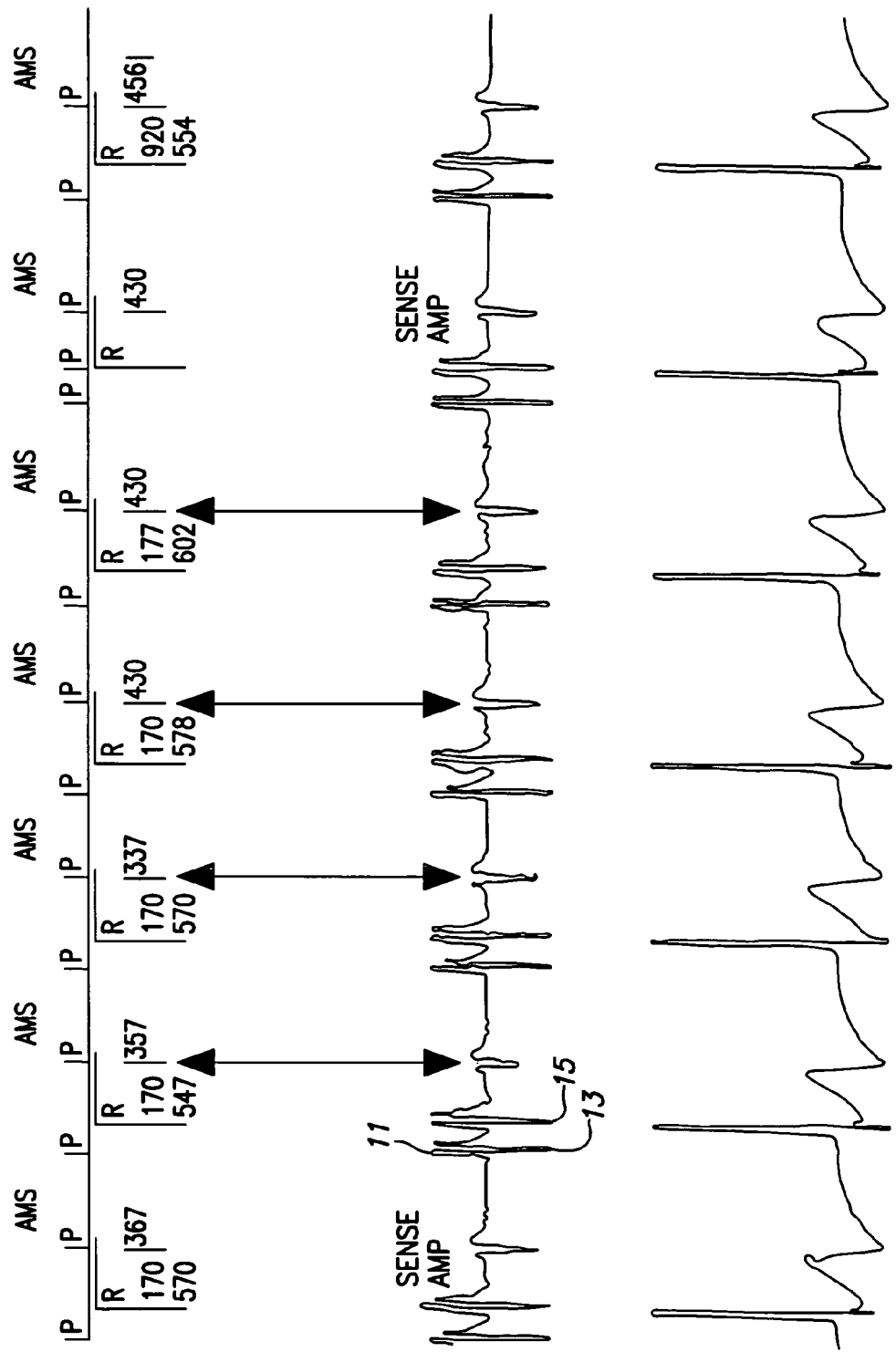
FIG. 3 is a graph illustrating a circumstance wherein an unnecessary mode switch is performed is a system employing atrial bipolar leads.
Figures 1, 9:
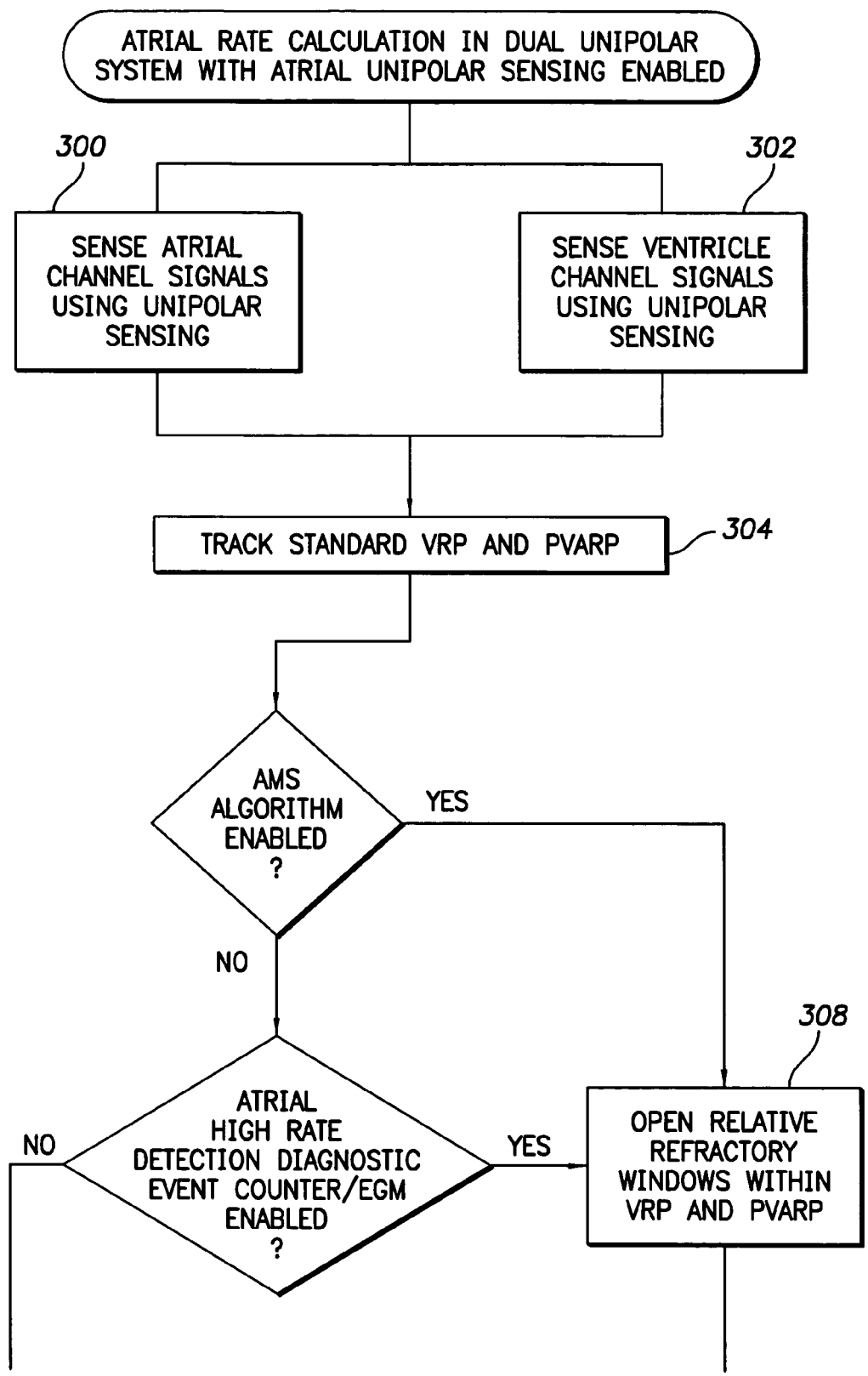
Figures 2, 9:
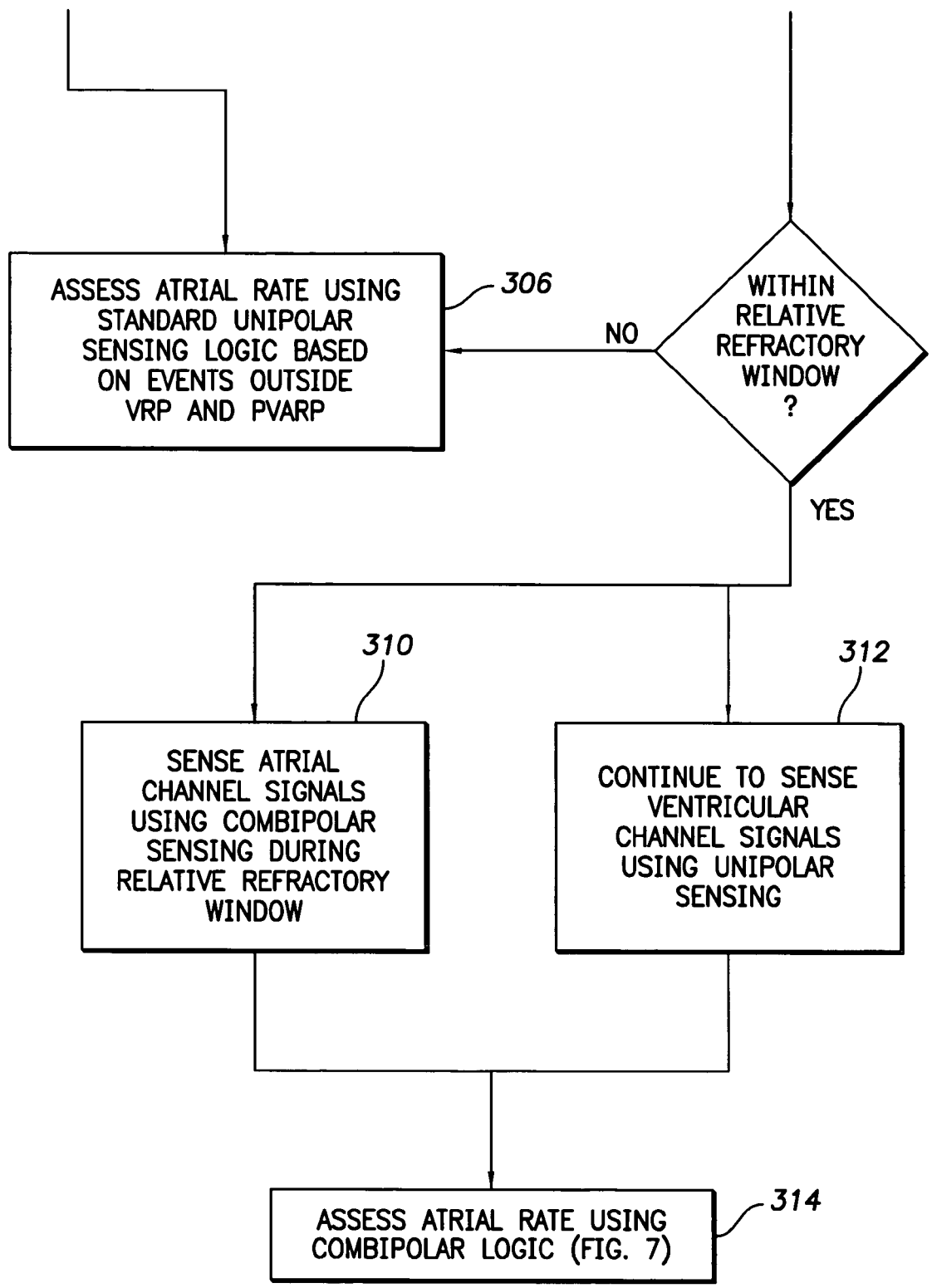

Referring now to FIGS. 9-1 and 9-2, a method for determining an atrial rate is provided for use by a pacemaker having dual unipolar leads but programmed to use unipolar sensing logic on both the atrial and ventricular channels. Combipolar logic is then selectively activated during refractory periods to improve atrial rate determination. Initially, at steps 300 and 302, the pacemaker senses atrial and ventricular channel EGM signals based on voltage differentials detected between the tips of the atrial and ventricular leads, respectively, and the body of the pacemaker in accordance with standard unipolar sensing. Thus, in contrast with the technique of FIG. 6, Combipolar sensing is not initially used on the atrial channel. As before, the pacemaker tracks a VRP on the ventricular channel and a PVARP on the atrial channel, step 304. Thereafter, processing depends on whether AMS is enabled and whether an atrial high rate diagnostic event counter/EGM is enabled. If AMS is not enabled and no atrial high rate diagnostic event counter/ EGM is enabled, then the atrial rate determination unit of the pacemaker determines the atrial rate at step 306 in accordance with standard unipolar sensing logic wherein any events occurring within PVARP and VRP are excluded.

However, if either AMS is enabled or an atrial high rate diagnostic event counter/EGM is enabled, then processing proceeds to step 308, wherein the pacemaker opens relative refractory windows in both the VRP and PVARP. (Note that, in some devices, relative windows are always open within the PVARP and VRP.) During the relative refractory windows, the pacemaker senses atrial channel signals using Combipolar sensing at step 310 while still sensing ventricular channel signals using unipolar sensing at step 312. Thus, for the atrial channel, sensing is automatically switched from unipolar sensing to Combipolar sensing for the duration of the relative refractory window. Then, the pacemaker updates the atrial rate at step 314 using the Combipolar sensing logic of FIG. 7. Thus, unipolar sensing is used outside the relative refractory windows of the VRP and PVARP whereas Combipolar sensing is used during the relative refractory windows of the VRP and PVARP, permitting more accurate detection of high atrial rates.

Although not specifically shown in FIGS. 9-1 and 9-2, after the atrial rate has been updated, a determination may be made as to whether the atrial rate exceeds the ATDR and, if so, a mode switch is triggered. Otherwise, the pacemaker instead continues its previous mode of operation. Processing ultimately returns to the beginning of FIG. 9-1 wherein additional signals are sensed and the atrial rate may be updated again.

Thus FIGS. 9-1 and 9-2 provide an overview of a technique for selectively activating Combipolar sensing during refractory periods within dual unipolar systems, which improves atrial rate calculation so as to reduce inappropriate mode switching during AMS. In the following, a technique is described for selectively activating Combipolar sensing during refractory periods within dual bipolar systems.

Dual Bipolar Lead System with Atrial Bipolar Sensing Enabled

Figures 1, 10:
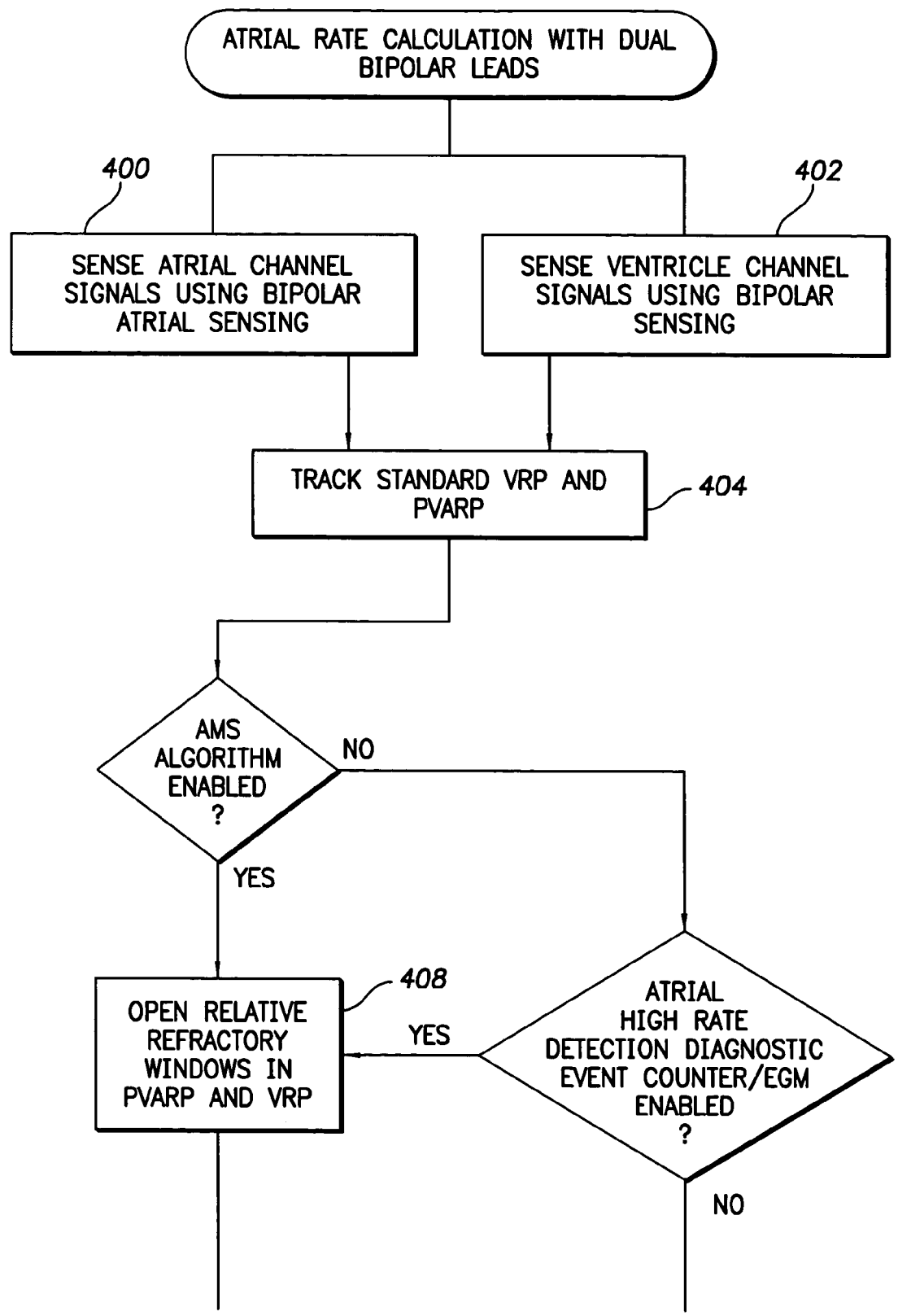
Figures 2, 10:
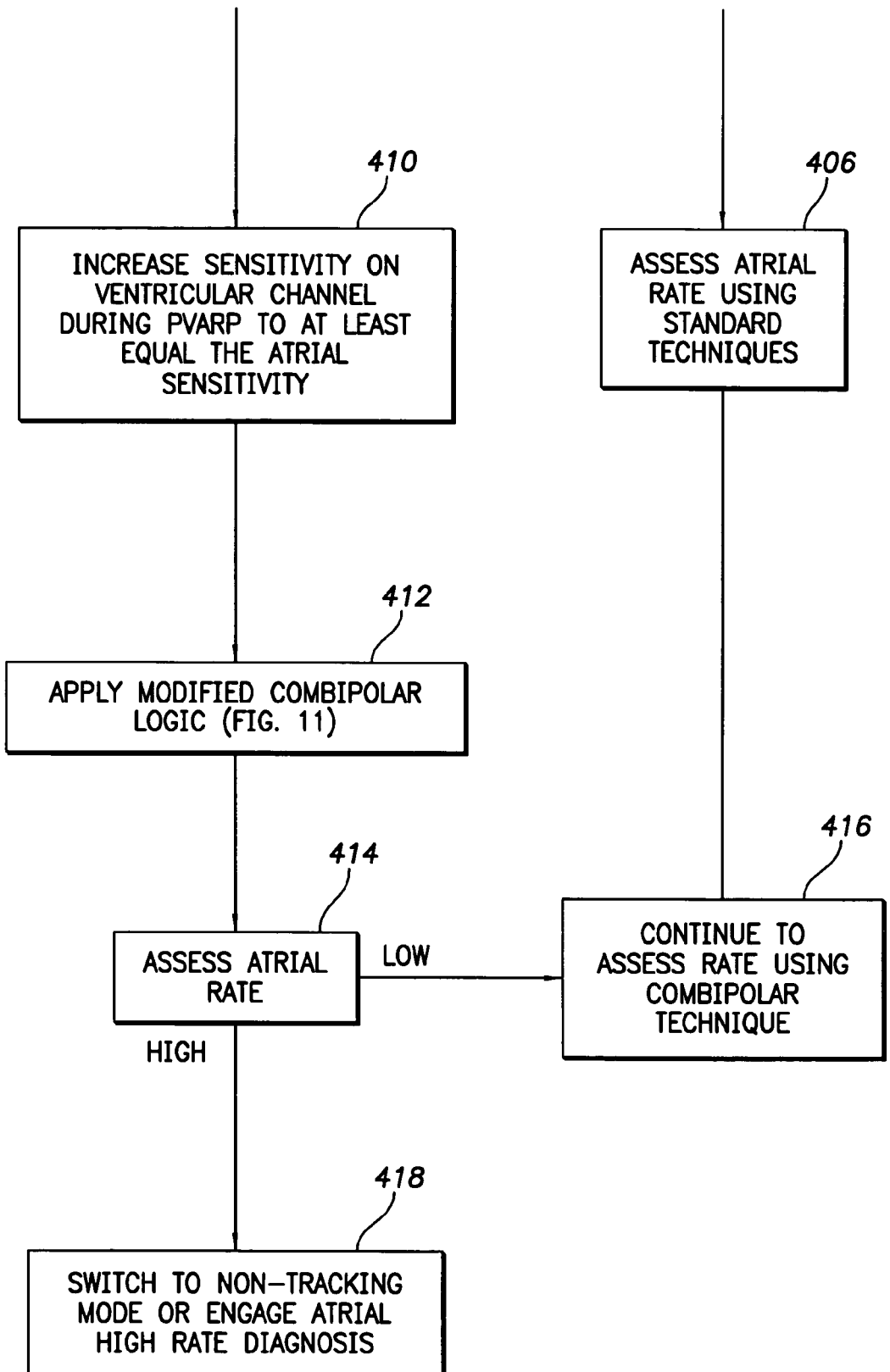

Referring now to FIGS. 10-1 and 10-2, a method for determining an atrial rate is provided for use by a pacemaker capable of bipolar atrial sensing. In the example, the device also employs bipolar ventricular sensing, though unipolar sensing may instead be employed in the ventricles. Initially, at steps 400 and 402, the pacemaker senses atrial and ventricular channel signals using bipolar sensing. As in the preceding embodiments, the pacemaker tracks a VRP on the ventricular channel and a PVARP on the atrial channel, step 404. Thereafter, processing depends on the current mode of operation. If AMS is not enabled and no atrial high rate diagnostic event counter/EGM is enabled, then the atrial rate is determined using standard techniques at step 406. Otherwise, relative refractory windows are opened in the PVARP and the VRP, step 408 and the sensitivity of the ventricular channel is increased during the PVARP so as to be at least equal to that of eh atrial channel, step 410. During the refractory periods, Combipolar sensing is then employed to detect P-waves, step 412. The Combipolar sensing technique employed is a modified Combipolar sensing technique, which is shown in FIG. 11 and is described below.

Once Combipolar sensing is activated, the atrial rate determined using Combipolar sensing is compared, at step 416, against the ATDR and, if the rate does not exceed the ATDR, the device continues to monitor the atrial rate, at step 416, using Combipolar sensing applied to events within the relative windows of the refractory periods and using bipolar sensing logic otherwise. If the rate exceeds the ATDR, then a mode switch is performed (if AMS is enabled) or an atrial high rate diagnosis is performed (if AMS is not enabled), at step 418.

Figure 11:
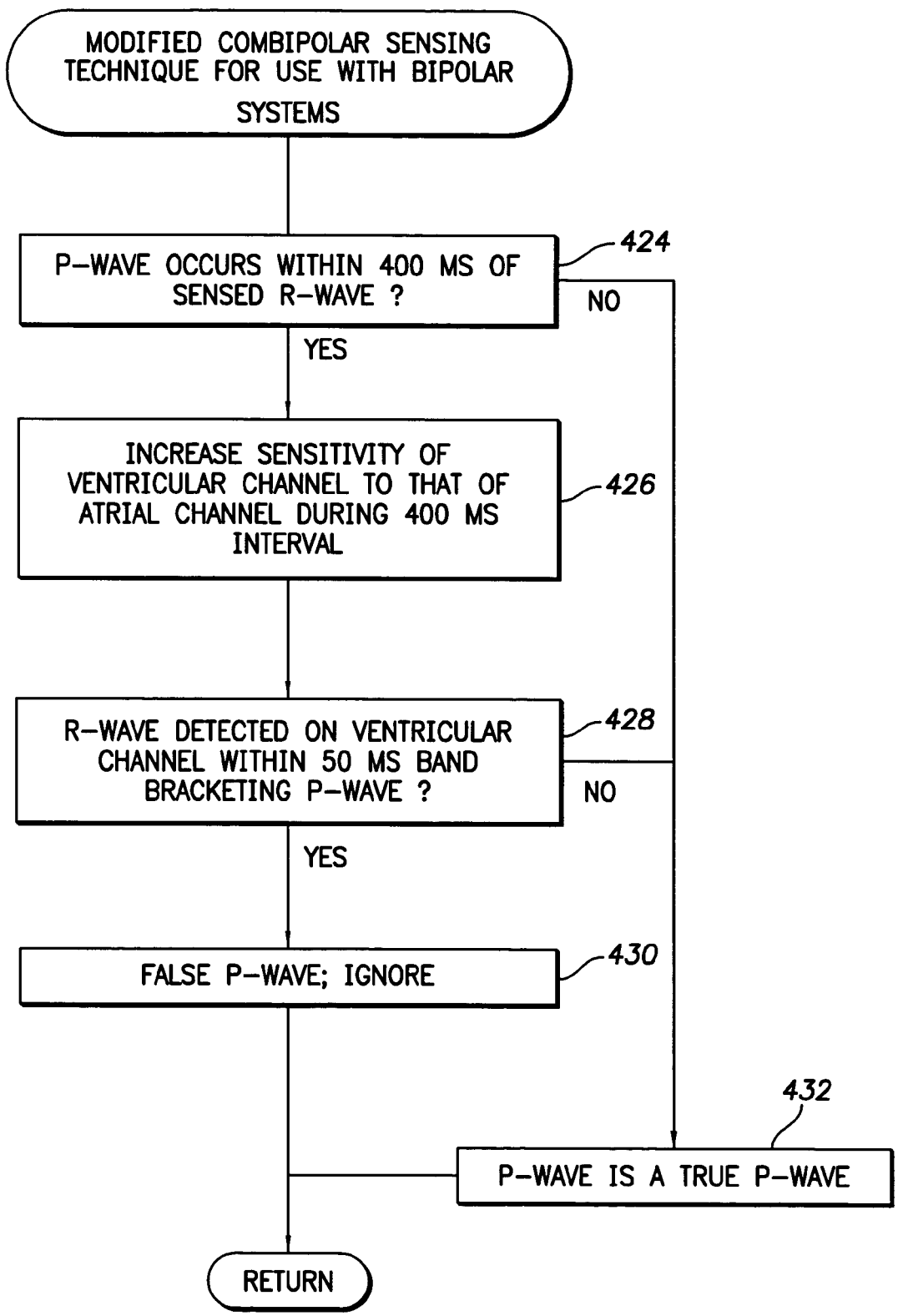
FIG. 11 is a flow chart illustrating an improved P-wave discrimination technique for use during Combipolar sensing with the bipolar lead method of FIGS. 10-1 and 10-2.

The modified Combipolar logic technique is set forth in the P-wave discrimination flowchart of FIG. 11. Briefly, at 424, the system determines whether the P-wave occurs within 400 milliseconds of a sensed R-wave. If not, the P-wave is deemed to be a true P-wave, at step 432. However, if so, the sensitivity of the ventricular channel is increased, at step 426, to that of the atrial channel during a 400 ms interval. Then, a determination is made as to whether the R-wave detected on the ventricular channel is within a 50 millisecond interval bracketing the P-wave. Again, if not, the P-wave is deemed to be a true P-wave, at step 432. However, if so, the P-wave is deemed to be a false P-wave and is instead ignored, at step 430. In any case, processing returns to FIGS. 10-1 once determination is made as to the nature of the detected P-wave.

As noted, the technique of FIGS. 10-1, 10-2, and 11 is provided to exploit Combipolar sensing logic in bipolar atrial systems to improved atrial rate detection. In particular, it helps compensate for possible oversensing of T-waves that should otherwise be filtered out. In this regard, one of the purposes of a refractory period is to prevent detection of known but inappropriate signals such as T-waves. Hence, the period of increase in ventricular sensitivity is preferably restricted to just those times when known but inappropriate signals are likely to occur. As the T-wave usually occurs between 200 to 300 ms after an R-wave, which is likely to be 300 to 400 ms after the previous P-wave, the period of increased sensitivity is restricted to a programmable window usually no more than 400 ms. To allow for long QT intervals, this window is programmable. With respect to the 50 ms bracket provided in FIG. 11, in Combipolar systems, ventricular events are detected at an identical time on the atrial and ventricular channel since the atrial detection circuit utilizes the ventricular electrode. In the dual-bipolar system, the two circuits are completely separate. As such, there may be a discrepancy between detection of the signal on one lead as compared to the other lead. Hence, a window is created such that if a ventricular event is detected within a window around the detected atrial event (e.g. 25 ms to either side), the "atrial event" will be treated as a true ventricular event and not used in the atrial rate calculation.

Also, note that a timing circuit may be provided on the atrial channel wherein a true detected R-wave occurring within a programmable time interval after a detected P-wave effectively cancels the use of that P-wave for detection purposes. The programmable interval is referred to as a pre-VAB. The use of the timing circuit and the pre-VAB may be employed in connection with the technique of FIG. 11 to aid in distinguishing between true and false P-waves. See U.S. Pat. No. 6,516,225 to Florio, entitled "System And Method For Distinguishing Electrical Events Originating In The Atria From Far-Field Electrical Events Originating In The Ventricles As Detected By An Implantable Medical Device", which is incorporated by reference herein.

Thus, FIGS. 10-1, 10-2, and 11 provide an overview of a technique for activating Combipolar sensing in bipolar atrial systems during refractory periods, which provides a more accurate assessment of the atrial rate. With the technique of FIGS. 10-1, 10-2, and 11 Combipolar sensing is activated regardless of the atrial rate. In the following, Combipolar sensing is only activated during the refractory period, if the atrial rate exceeds a predetermined threshold.

Figures 1, 12:
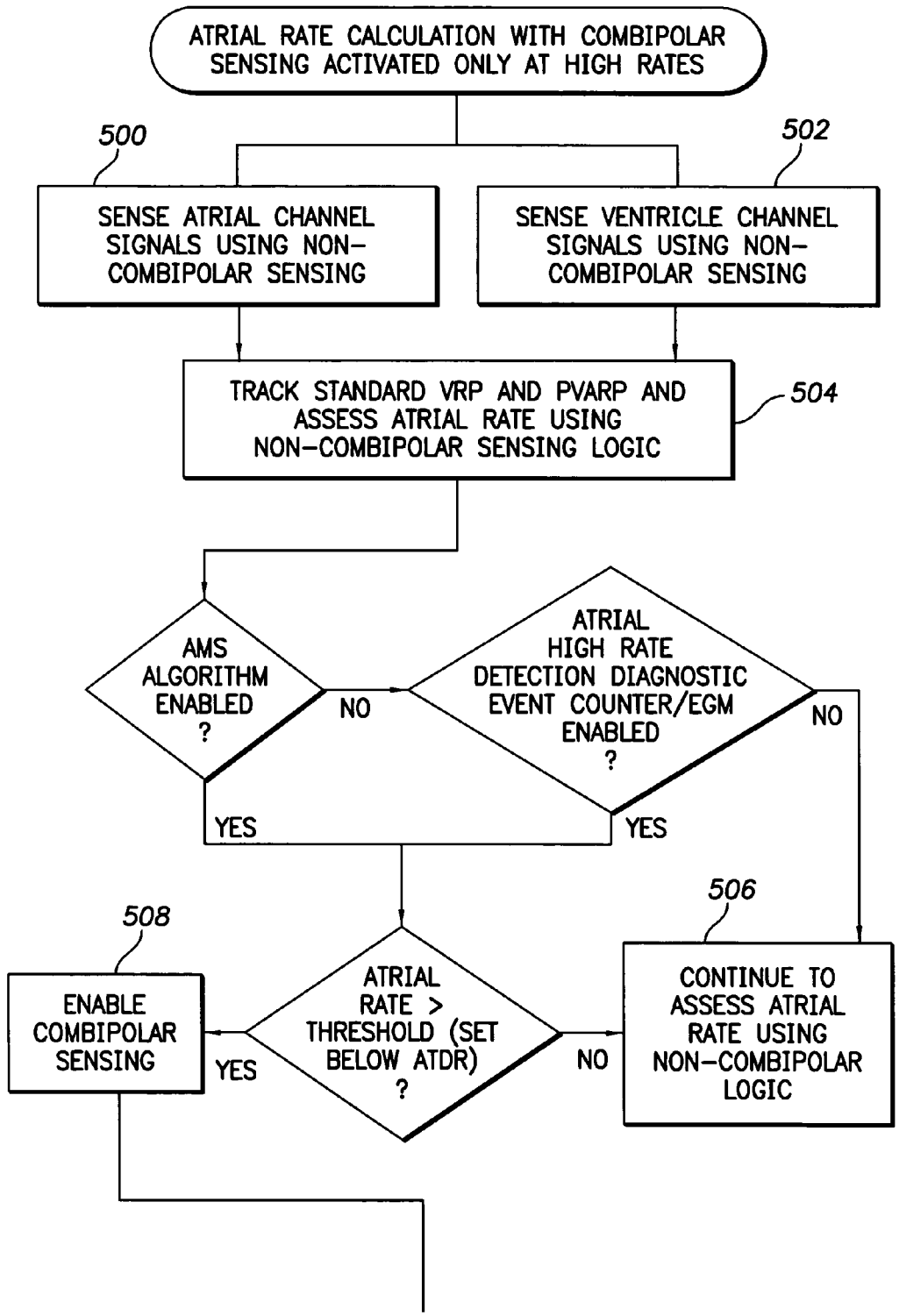
Figures 2, 12:
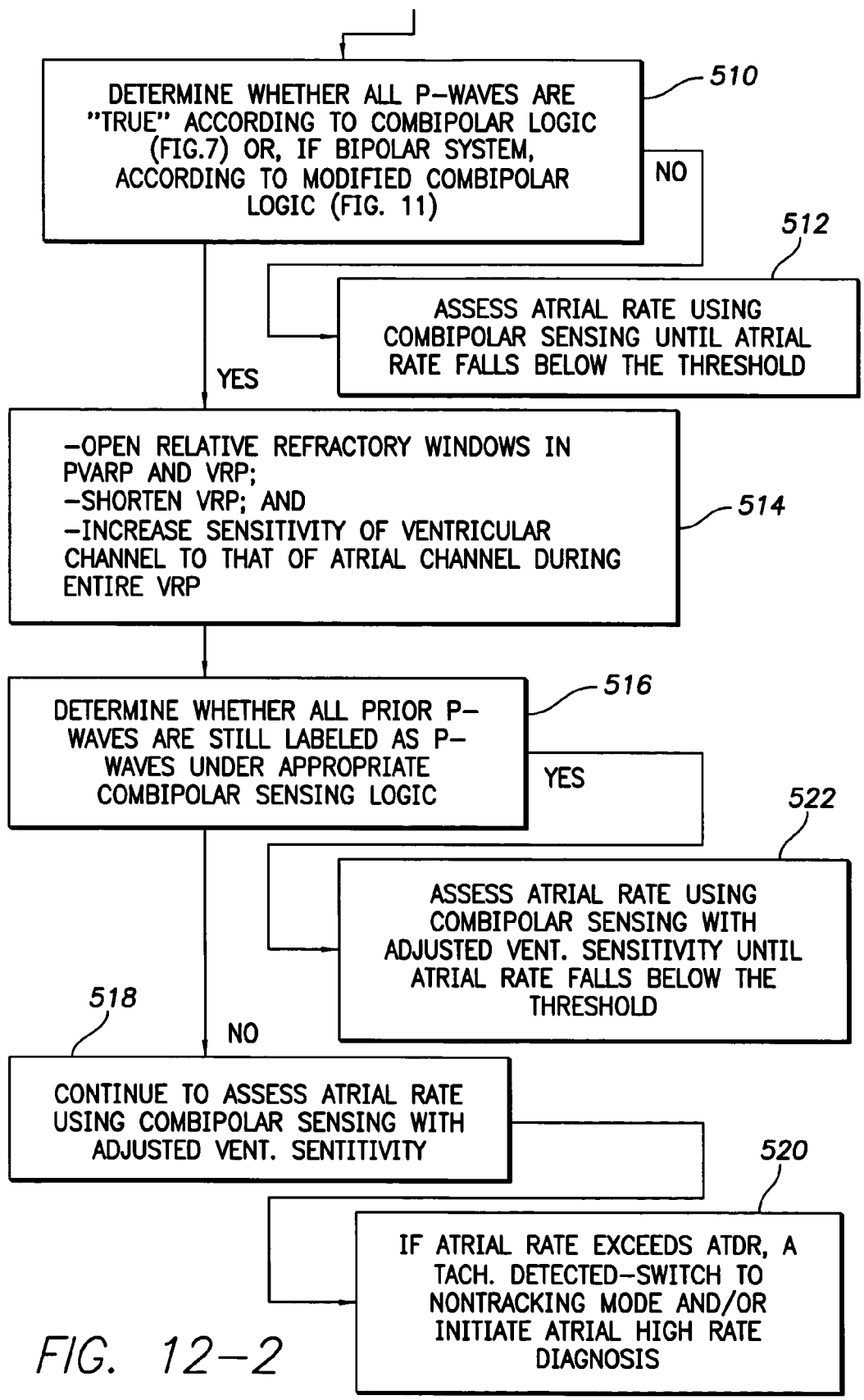

Activation of Combipolar Sensing in Dual Unipolar or Dual Bipolar Systems Based on Atrial Rate Referring now to FIGS. 12-1 and 12-2, a method for determining an atrial rate is provided for use by a pacemaker ordinarily programmed to use a non-Combipolar sensing technique, such as bipolar or unipolar sensing. Initially, at steps 500 and 502, the pacemaker senses atrial and ventricular channel signals. As in the preceding embodiments, the pacemaker tracks a VRP on the ventricular channel and a PVARP on the atrial channel, step 504. Thereafter, processing depends on the current mode of operation. If AMS is not enabled and no atrial high rate diagnostic event counter/ EGM is enabled, then the atrial rate is determined using non-Combipolar techniques at step 506. Otherwise, the atrial rate is compared against a preset or programmable threshold set below the ATDR. In one example, the threshold is set 20 to 30 bpm below the ATDR. In another, it is set to a fixed value somewhere below the ATDR. So long as the atrial rate remains below the threshold, the pacemaker simply continues to monitor the atrial rate using non-Combipolar techniques, at step 506. However, if the atrial rate exceeds the threshold, then Combipolar sensing is enabled, at step 508, and relative refractory windows are opened in the PVARP and VRP for sensing, if not already done so.

Next, at step 510, the device determines whether all P-waves that have been identified are "true" P-waves according to Combipolar sensing logic. If the device employs a bipolar lead, the modified Combipolar logic of FIG. 11 is instead employed. Otherwise, the standard Combipolar logic of FIG. 7 is employed. In any case, if all P-waves are not "true" according to the selected form of Combipolar logic, then the device continues to monitor the atrial rhythm using Combipolar logic until the atrial rate falls below the preset threshold, step 512, after which normal non-Combipolar sensing resumes. In other words, if at least some of the P-waves are actually far-field ventricular events, Combipolar sensing continues so that the Combipolar logic can eliminate the far-field events from the atrial rate calculation. If, however all of the P-waves are deemed to be true P-waves according to Combipolar sensing logic, then step 514 is instead performed wherein the VRP is shortened and opened for sensing (if not already opened). In addition, during the shortened VRP, the sensitivity of the ventricular channel is increased to be at least equal to that of the atrial channel. Then, at step 516, the device reassesses the atrial signals by determining whether all prior P-waves are still labeled as P-waves under Combipolar sensing logic. If not, the device continues to monitor the atrial rhythm using Combipolar logic, at step 518, and then compares, at step 520, the atrial rate against the ATDR and engages AMS and initiates atrial high rate detection, if the atrial rate exceeds the ATDR. However if all of the prior P-waves are still labeled as P-waves despite the changes in the ventricular sensitivity and the VRP length, then step 522 is instead performed wherein the device continues to monitor the atrial rate using the modified system until the atrial rate falls below the threshold value, after which normal non-Combipolar sensing may be reactivated. In other words, a mode switch is not performed and high rate diagnosis is not activated. These steps are taken so as to account for the possibility that T-waves are not properly being filtered and are being misidentified as "true" P-waves.

Thus FIGS. 12-1 and 12-2 provide an overview of a technique for exploiting Combipolar sensing in non-Combipolar systems, which triggers Combipolar sensing based, in part, on atrial rate so as to provide a more accurate assessment of the atrial rate. In the specific example of FIGS. 12-1 and 12-2, Combipolar sensing is activated if the atrial rate exceeds a threshold, typically set below the ATDR. The reason for not waiting until the atrial rate reaches the ATDR is that the standard AMS algorithm switches to a nontracking mode as soon as the ATDR is achieved. As such, the device should begin to monitor for inappropriate signals at a lower rate. If these are detected, the events will no longer be labeled P-waves and a filtered atrial rate derived from the atrial events will begin to slow precluding reaching ATDR in response to an inappropriate signal. An alternative approach is to arbitrarily begin to look for these signals at a programmable rate (e.g. 150 bpm) even if the ATDR is programmed to a significantly higher rate. If the ATDR is programmed to a rate below 150 bpm, the likelihood of a far-field T-wave being misinterpreted as an atrial event to falsely increase the filtered atrial rate is remote because the T-wave will not occur that far out from the previous true P-wave.

What have been described are various exemplary techniques for improved atrial rate determination within implantable cardiac stimulation devices. The embodiments described herein are merely illustrative and should not be construed as limiting the scope of the invention, which is to be interpreted in accordance with the claims that follow.

What is claimed is:

1. In an implantable cardiac stimulation device having an atrial bipolar lead and at least one ventricular lead, a method for determining an atrial rate comprising:
   tracking refractory periods within both the atrial and ventricular channel signals; and
   determining an atrial rate using bipolar sensing outside the refractory periods and using combined unipolar/ bipolar sensing within the refractory periods.

2. The method of claim 1 wherein determining the atrial rate using bipolar sensing outside the refractory periods and using combined unipolar/bipolar sensing within the refractory periods is only performed if automatic mode switching (AMS) is enabled in the implantable stimulation device or if an atrial high rate detection diagnostic event counter is enabled, otherwise the atrial rate is determined based only on events outside the refractory periods sensed via bipolar sensing.

3. The method of claim 1 further comprising increasing a ventricular sensitivity during the refractory periods to at least equal that of an atrial sensitivity.

4. The method of claim 3 wherein updating the atrial rate based on events detected inside the refractory periods using combined unipolar/bipolar sensing employs a modified combined unipolar/bipolar sensing logic comprising:
   detecting R-waves on the ventricular channel;
   detecting candidate P-waves on the atrial channel;
   determining whether the candidate P-waves occur within a first period of time bracketing detected R-waves; and
   if not, concluding the candidate P-waves are true P-waves; and
   if so, increasing a sensitive on the ventricular channel to equal a sensitivity on the atrial channel during the period of time bracketing the R-waves and determining R-waves are detected on the ventricular channel within a second, shorter, period of time bracketing the P-waves.

5. The method of claim 4 further comprising:
   concluding that the candidate P-waves are true P-waves if R-waves are not detected on the ventricular channel within the second, shorter, period of time bracketing the P-waves; and
   concluding that the candidate P-waves are false P-waves otherwise.

6. The method of claim 5 wherein the first period of time bracketing detected R-waves is about 400 milliseconds (ms) and the second period of time bracketing the P-waves is about 50 ms.

7. The method of claim 1 further comprising opening relative refractory windows within the atrial and ventricular refractory periods and wherein the step of determining the atrial rate using combined unipolar/bipolar sensing within the refractory periods only applies to events within the relative refractory windows of the refractory periods.

8. The method of claim 7 wherein tracking atrial and ventricular relative refractory windows within the atrial and ventricular signals comprises:
   detecting an R wave on the ventricular channel;
   initiating atrial and ventricular blanking intervals on the atrial and ventricular channels, respectively, following detection of the R wave for a predetermined blanking period of time; and
   initiating atrial and ventricular relative refractory windows on the atrial and ventricular channels, respectively, immediately following completion of the atrial and ventricular blanking intervals for a predetermined relative refractory duration of time.

9. The method of claim 8:
   wherein the ventricular blanking interval has a duration shorter than an average R-T interval occurring during normal sinus rhythm; and
   wherein the ventricular blanking interval and the relative refractory window together have a combined duration longer than the average R-T interval of normal sinus rhythm such that the T-wave typically occurs during the ventricular relative refractory window.

10. The method of claim 8 wherein the atrial blanking interval has a duration equal to the ventricular blanking interval and the atrial relative refractory window has a duration equal to the ventricular relative refractory window such that the T-wave typically occurs during the atrial relative refractory window.

11. The method of claim 1 further comprising comparing the updated atrial rate against atrial tachycardia detection threshold (ATDR) threshold and performing a mode switch if automatic mode switching (AMS) is enabled and if the rate crosses the ATDR threshold.

12. The method of claim 1 further comprising comparing the updated atrial rate against atrial tachycardia detection threshold (ATDR) threshold and initiating an atrial high rate diagnosis procedure if automatic mode switching (AMS) is not enabled and if the rate exceeds the ATDR threshold.

13. The method of claim 1 further comprising comparing the updated atrial rate against atrial tachycardia detection threshold (ATDR) threshold and continuing to asses the atrial rate using combined unipolar/bipolar sensing so long as the rate does not exceed the ATDR threshold.

14. In an implantable cardiac stimulation device having an atrial bipolar lead and at least one ventricular lead, a system comprising:
   an atrial sense amplifier operative to sense atrial channel signals;
   a ventricular sense amplifier operative to sense ventricular channel signals;
   a control unit operative to track refractory periods within atrial and ventricular channel signals; and
   an atrial rate determination unit programmed to determine an atrial rate using bipolar sensing outside the refractory periods and using combined unipolar/bipolar sensing within the refractory periods.

15. In an implantable cardiac stimulation device having an atrial bipolar lead and at least one ventricular lead, a system comprising:
   means for tracking refractory periods within both the atrial and ventricular channel signals; and
   means programmed to determine an atrial rate using bipolar sensing outside the refractory periods and using combined unipolar/bipolar sensing within the refractory periods.

* * * * *